United States Patent
Makino et al.

(10) Patent No.: US 9,964,520 B2
(45) Date of Patent: May 8, 2018

(54) SURFACE PROPERTY INSPECTION DEVICE AND METHOD

(71) Applicant: SINTOKOGIO, LTD., Nagoya-shi, Aichi (JP)

(72) Inventors: Yoshiyasu Makino, Toyokawa (JP); Kazuhiro Ota, Toyokawa (JP); Hideaki Kaga, Toyokawa (JP)

(73) Assignee: SINTOKOGIO, LTD., Aichi (JP)

(*) Notice: Subject to any disclaimer, the term of this patent is extended or adjusted under 35 U.S.C. 154(b) by 0 days. days.

(21) Appl. No.: 15/112,473

(22) PCT Filed: Sep. 19, 2014

(86) PCT No.: PCT/JP2014/074845
§ 371 (c)(1),
(2) Date: Jul. 19, 2016

(87) PCT Pub. No.: WO2015/107725
PCT Pub. Date: Jul. 23, 2015

(65) Prior Publication Data
US 2016/0341699 A1   Nov. 24, 2016

(30) Foreign Application Priority Data

Jan. 20, 2014 (JP) .................. 2014-007788
Feb. 12, 2014 (JP) .................. 2014-024198

(51) Int. Cl.
*G01N 27/90* (2006.01)

(52) U.S. Cl.
CPC ......... *G01N 27/9046* (2013.01); *G01N 27/90* (2013.01); *G01N 27/9086* (2013.01)

(58) Field of Classification Search
CPC ........ G01N 27/72; G01N 27/80; G01N 27/82; G01N 27/90; G01N 27/9006;
(Continued)

(56) References Cited

U.S. PATENT DOCUMENTS 3,539,006 A   11/1970 Hanna et al.
4,742,298 A * 5/1988 Ando ................. G01N 27/9046
                                                          324/220
(Continued)

FOREIGN PATENT DOCUMENTS

JP   S 55-7630 A   1/1980
JP   H 10-78411 A   3/1998
(Continued)

OTHER PUBLICATIONS

International Search Report, and English language translation thereof, in corresponding International Application No. PCT/JP2014/074845, dated Dec. 22, 2014, 5 pages.
(Continued)

*Primary Examiner* — Huy Q Phan
*Assistant Examiner* — David Frederiksen
(74) *Attorney, Agent, or Firm* — Brinks Gilson & Lione

(57) ABSTRACT

To provide a surface property inspection device and method capable of inspecting the surface treatment state of treated material subjected to surface treatments. A surface property inspection device 1 includes an AC power supply 10, an AC bridge circuit 20, and an evaluation apparatus 30, and the AC bridge circuit 20 is formed by a variable resistor 21 with a distribution ratio of γ, a reference detector 22, and an inspection detector 23. The inspection detector 23 includes a coil 23*b* wound so as to oppose the surface property inspection area of the test object M; an eddy current is excited in the test object M by supplying AC power to the coil 23*b*. A reference test object S with the same structure as the test object M is placed in the reference detector 22 to cancel inspection environment effects.

8 Claims, 13 Drawing Sheets

(58) Field of Classification Search
CPC ........... G01N 27/9033; G01N 27/9046; G01N 27/9073; G01N 27/9086; G01B 7/06; G01B 7/10; G01B 7/105; C21D 7/06; C21D 11/00

See application file for complete search history.

(56) References Cited

U.S. PATENT DOCUMENTS

| | | | |
|---|---|---|---|
| 5,537,037 A * | 7/1996 | Otaka | G01N 27/82 |
| | | | 324/225 |
| 5,793,199 A | 8/1998 | Kasahara et al. | |
| 5,898,302 A | 4/1999 | Soules | |
| 6,377,039 B1 * | 4/2002 | Goldfine | G01B 7/105 |
| | | | 324/207.17 |
| 9,638,668 B2 * | 5/2017 | Makino | G01N 27/9046 |
| 2003/0030433 A1 | 2/2003 | Migliori et al. | |
| 2004/0095135 A1 * | 5/2004 | Nejikovsky | B61K 9/08 |
| | | | 324/217 |
| 2007/0163712 A1 * | 7/2007 | Gotkis | G01B 7/105 |
| | | | 156/345.1 |
| 2008/0001609 A1 | 1/2008 | Kojima et al. | |
| 2008/0191693 A1 * | 8/2008 | Jones | G01D 5/243 |
| | | | 324/238 |
| 2013/0009632 A1 * | 1/2013 | Yamamoto | G01N 27/9046 |
| | | | 324/222 |
| 2014/0084910 A1 | 3/2014 | Makino | |

FOREIGN PATENT DOCUMENTS

| | | |
|---|---|---|
| JP | 2005-331332 A | 12/2005 |
| JP | 2008-2973 A | 1/2008 |
| JP | 2009-36682 A | 2/2009 |
| JP | 2009036682 A * | 2/2009 |
| JP | 2009-168556 A | 7/2009 |
| JP | 2009-236679 A | 10/2009 |
| JP | 2009236679 A * | 10/2009 |
| JP | 2011-2471 A | 1/2011 |
| JP | 2011002471 A * | 1/2011 |
| JP | 2013-529286 A | 7/2013 |

OTHER PUBLICATIONS

Extended European Search Report in corresponding European Application No. 14878820.1, dated Oct. 16, 2017, 8 pages.

* cited by examiner

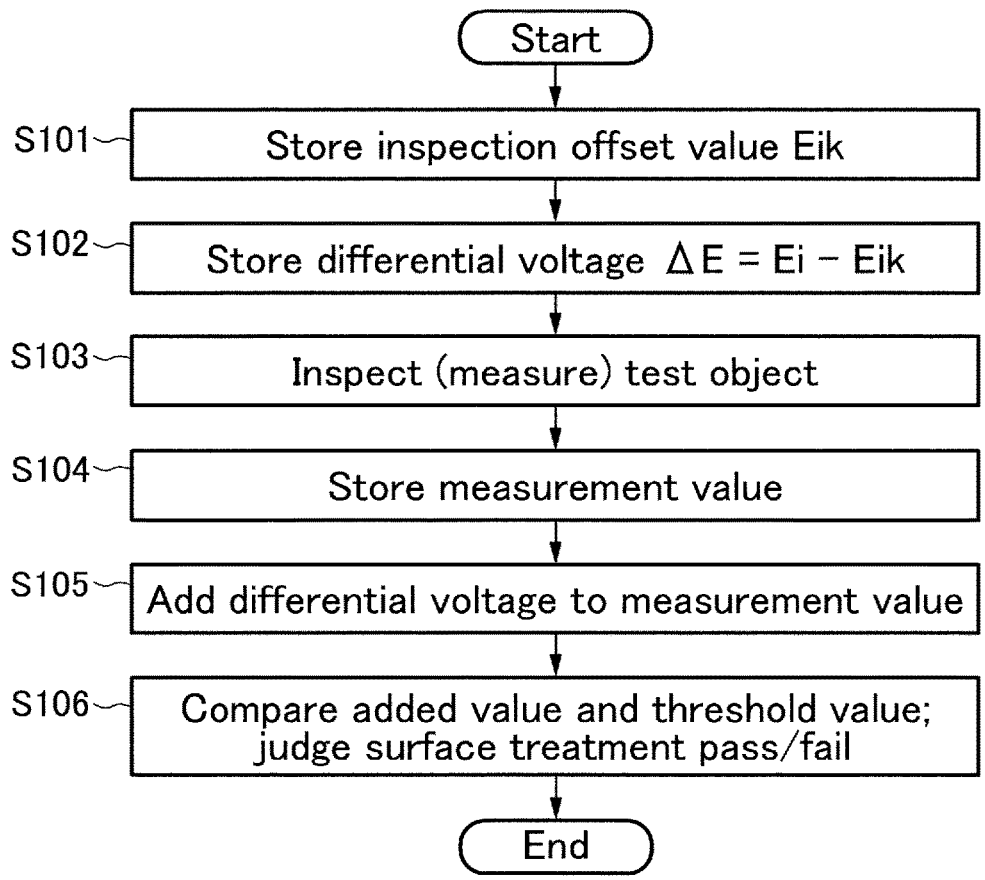

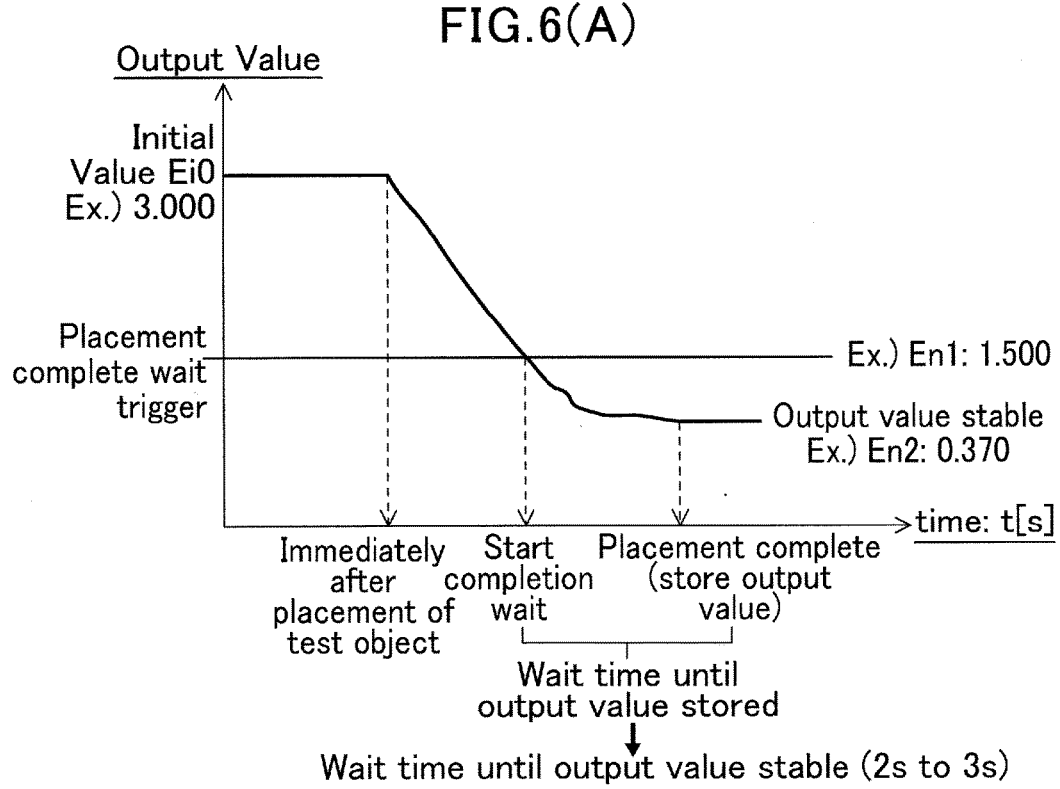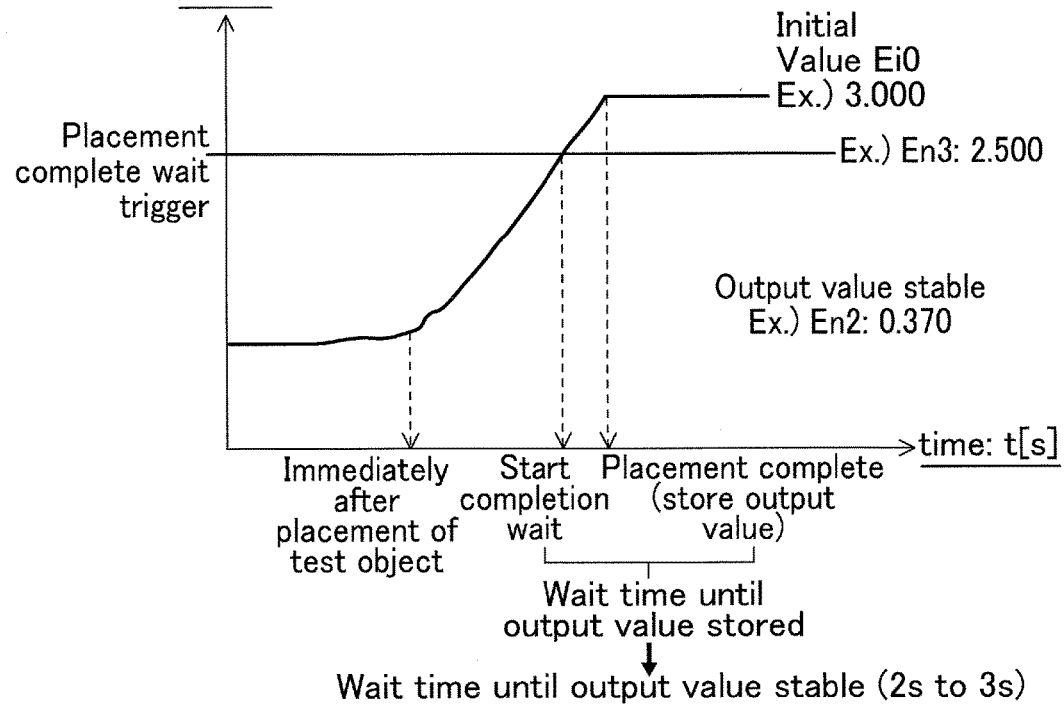

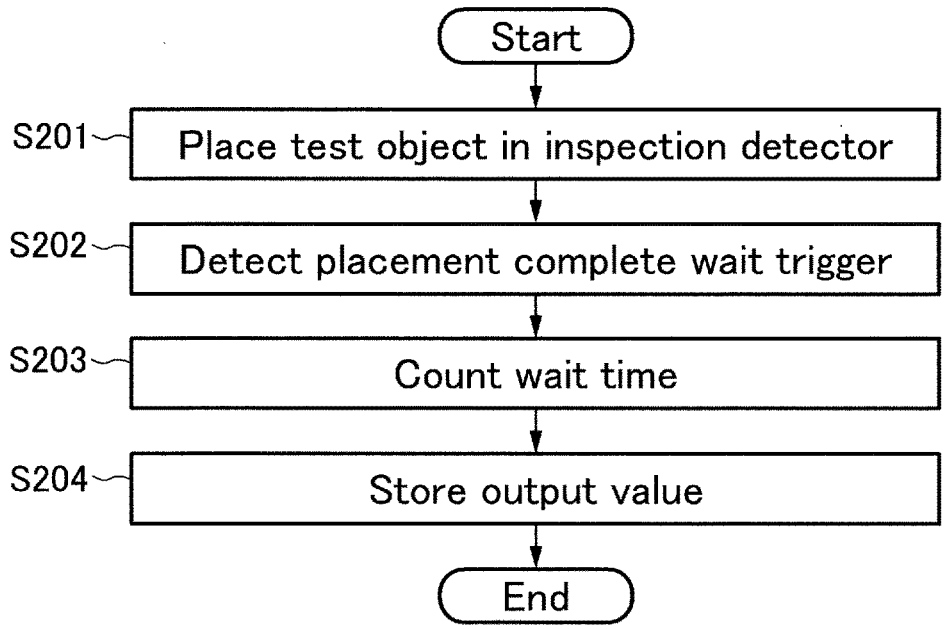
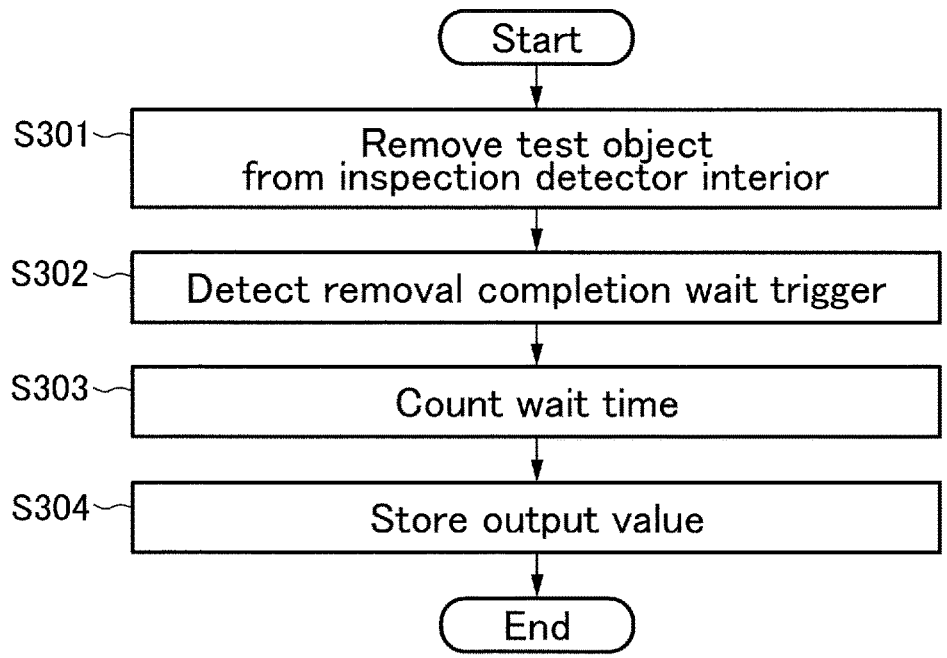

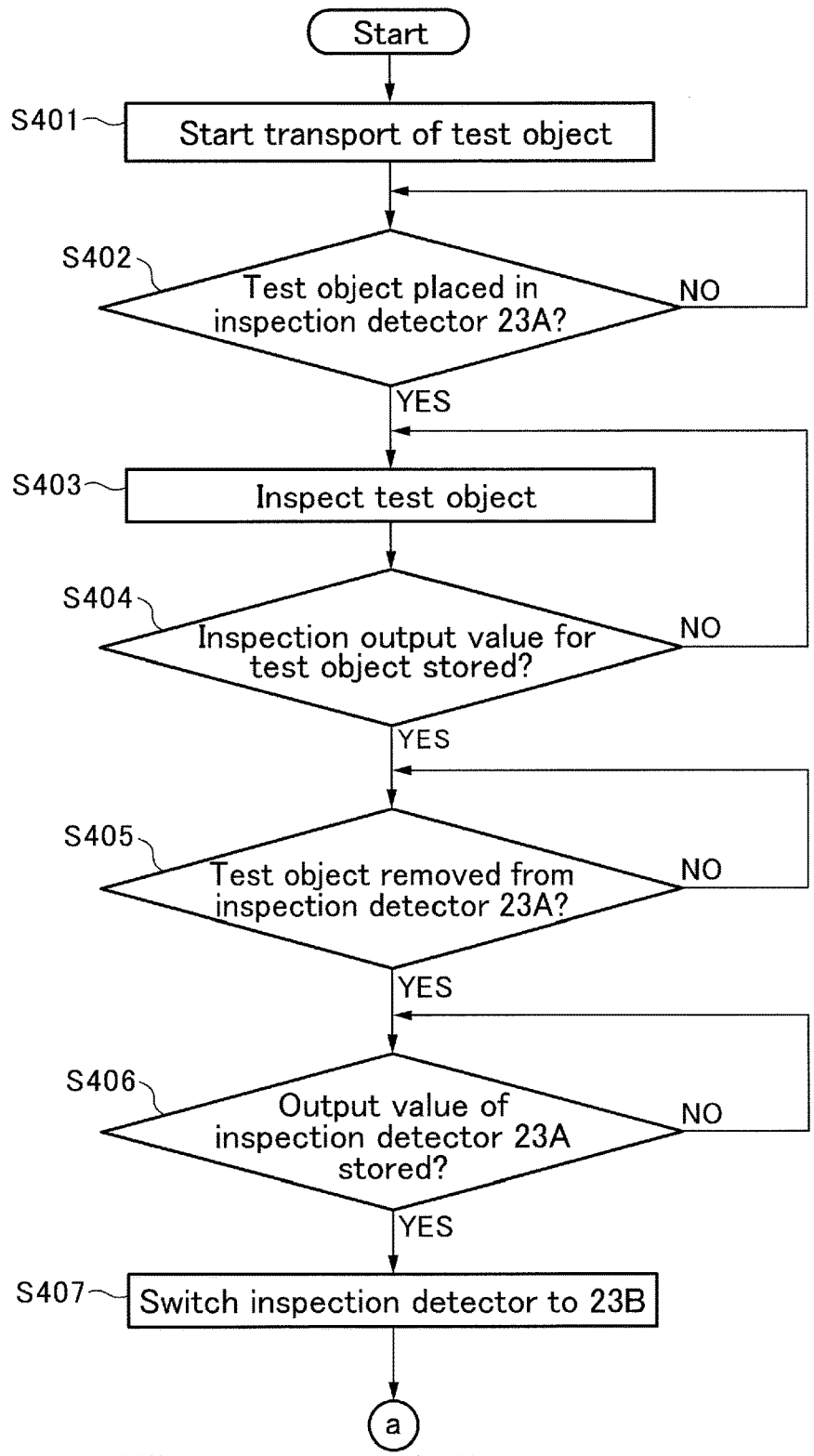

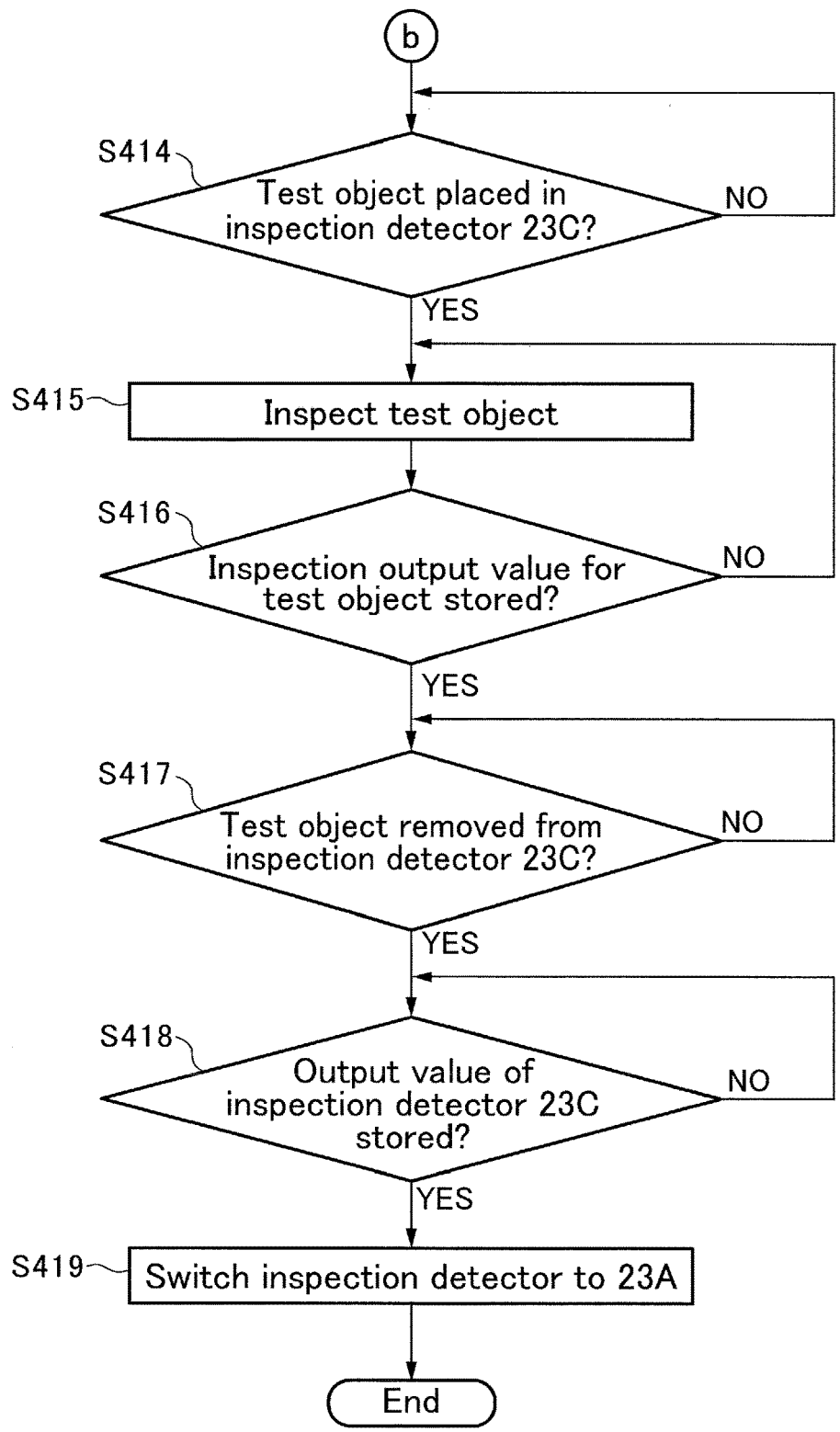

SURFACE PROPERTY INSPECTION DEVICE AND METHOD

This application is a 371 application of PCT/JP2014/074845 having an international filing date of Sep. 19, 2014, which claims priority to JP2014-007788 filed Jan. 20, 2014 and JP2014-024198 filed Feb. 12, 2014. The entire contests of these applications are incorporated herein by reference.

TECHNICAL FIELD

The present invention pertains to a surface property inspection device and surface property inspection method for non-destructive inspection of the surface treatment state of processed material subjected to surface treatment such as shot-peening, heat treatment, or nitriding.

BACKGROUND ART

Surface treatment such as surface hardening by heat treatment, nitriding, etc., or shot-peening or the like are applied to steel parts such as gears and shafts used as automobile parts or the like to improve friction resistance, fatigue strength, or the like.

Conventionally, evaluation of surface properties such as residual stress and hardness following surface treatment of such products has been performed by sample destructive inspection. This led to the problem that not all products could be directly inspected, and inspected products became unusable, since inspection was destructive.

This has led to an increased need to develop a device capable of non-destructively inspecting product surface properties. As an example of such a device, Patent Citation 1 discloses a non-destructive inspection device for a shot-peened surface, wherein an AC (alternating current) signal is input while varying the frequency to an inspection circuit comprising a coil disposed above a shot-peened surface, and the state of occurrence of residual stress in the inspected object is inspected using impedance frequency response characteristics of the inspection circuit.

PRIOR ART REFERENCES

Patent References

Patent Document 1: Japanese Published Unexamined Patent Application: 2008-2973

SUMMARY OF THE INVENTION

Problems to be Solved by the Invention

However, because elements of the electromagnetic measurement of magnetic permeability and conductivity, etc., which vary depending on surface treatment, are affected by environmental changes, the problem in the device set forth in Japanese Published Unexamined Patent Application 2008-2973 was that measurement errors could easily arise when the environment in which a reference test object was measured differed from the environment in which a test object was measured, particularly when temperature changes occurred. Also, there is no method disclosed for calibrating measurement values in a manner which accounts for those measurement errors.

The present invention therefore has the object of providing a surface property inspection device and surface property inspection method capable of inspecting the surface treatment state of treated material subjected to surface treatments such as shot-peening, heat treatment, nitriding and the like, with reduced effect from temperature or other changes in the inspection environment, and with good accuracy.

Means for Resolving Problems

To achieve the above object, the first aspect of the present invention uses a technical, being a surface property inspection device for inspecting surface property of a test object subjected to surface treatment, comprising: an AC bridge circuit; an AC power supply for supplying AC power to the AC bridge circuit; and an evaluation apparatus for evaluating the surface property of the test object based on an output signal from the AC bridge circuit; wherein the AC bridge circuit has a variable resistor capable of varying the distribution ratio between a first resistor and a second resistor, an inspection detector comprising a coil capable of exciting AC magnetism and formed so that said coil excites an eddy current in the test object, and a reference detector constituted to excite the eddy current in a reference test object having the same structure as the test object for detecting a reference state serving as a reference for comparison with the output from the inspection detector, whereby the first resistor, the second resistor, the reference detector, and the inspection detector constitute a bridge circuit; and wherein the evaluation apparatus evaluates surface property of the test object by comparing an output signal from the AC bridge circuit with a predetermined threshold value while AC power is supplied to the AC bridge circuit, the inspection detector detects electromagnetic property of the test object, and the reference detector detects the reference state.

With the first aspect of the present invention, an eddy current is excited in a test object by an inspection detector coil, and surface properties of the test object are evaluated by comparing the output signal output from an AC bridge circuit with a threshold value. This enables high precision inspection of the surface state with a simple circuit configuration. A method is adopted in which an eddy current is excited in the test object to inspect surface properties, therefore the effects of temperature variations on the inspection environment can be reduced. Since a reference test object of the same structure as the test object is used to detect a reference state in a reference detector, fluctuations in output values due to changes in the inspection environment such as temperature, humidity, and magnetism, will be the same on the reference detector as on the test object. Fluctuations in output values caused by changes in the inspection environment such as in temperature, humidity, or magnetism can thus be canceled, improving measurement accuracy. Here the term "same structure" means same materials and shape, whether or not surface treatment is applied.

Also, "surface properties" means "properties from the most superficial to the affected layer on the inside surface."

The second aspect of the present invention uses a technical means whereby in the first aspect of the present invention, surface property inspection device, the inspection detector comprises the coil wound to surround a surface property inspection area of the test object, and the eddy current is excited in the test object by supplying the coil with AC power from the AC power supply to detect electromagnetic property of the test object.

With the second aspect of the present invention, magnetism can be stably supplied to the test object, and the surface properties inspection area of the test object can be inspected in one pass. Also, dispersion of eddy currents and heat emission from the surface of the test object can be constrained, therefore temperature changes in the test object can be reduced and a higher accuracy inspection achieved.

The third aspect of the present invention uses a technical means whereby in the surface property inspection device set forth in either the first or second aspect of the present invention, the reference test object is an untreated object to which surface treatment has not been applied.

As in the third aspect of the present invention, use of an untreated part to which no surface treatment has been applied as the reference test object enables an increased output, which is based on the difference in surface state relative to the test object, therefore measurement accuracy can be still further improved and a threshold value more easily set, which is preferred.

The fourth aspect of the present invention uses a technical means whereby the surface property inspection device of any one of the first through third aspects of the present invention, the surface property inspection device includes plurality of the inspection detector, and further comprising a switching device capable of switching between which of said inspection detectors is connected to the bridge circuit.

The fourth aspect of the present invention comprises multiple inspection detectors, and inspections of objects under test can be conducted in sequence using a switching device by switching between inspection detectors constituting a bridge circuit, therefore the time required from transport to completion of inspection can be shortened. In addition, equipment cost can be reduced as an AC power supply and an evaluation apparatus are shared, and there is no requirement to prepare multiple surface property inspection device stands.

The fifth aspect of the present invention uses a technical means, being a method for inspecting surface property, comprising steps of: providing the surface property inspection device of any one of the first through fourth aspects of the present invention; a placement step for placing the inspection detector at a predetermined position relative to the test object so that the eddy current is excited in the test object when AC power is supplied from the AC power supply to the AC bridge circuit; and an evaluation step for evaluating surface property of the test object by comparing an output signal output from the AC bridge circuit with the threshold value while the reference test object is disposed in the reference detector; wherein the placement step and the evaluation step are executed for each test object.

With the fifth aspect of the present inventions, the surface property inspection device of any one of the first through fourth aspects of the present invention is prepared, an eddy current is excited in the test object by the inspection detector, and an output signal output from the AC bridge circuit is compared to a threshold value, with the reference test object disposed in the reference detector, to evaluate the surface properties of the test object. Because a reference test object of the same structure as the test object is used to detect a reference state in a reference detector, fluctuations in output values due to changes in the inspection environment such as temperature, humidity, and magnetism, will be the same on the reference detector as on the test object. Fluctuations in output values caused by changes in the examination environment, such as in temperature, humidity, or magnetism can thus be canceled, improving measurement accuracy.

The sixth aspect of the present invention uses a technical means whereby in the surface property inspection method of the fifth aspect of the present invention, an initial threshold value Ethi is used as the threshold value when starting evaluation of the test object, the initial threshold value Ethi is determined based on an output signal EA obtained when an untreated object is disposed in the inspection detector, and an output signal EB obtained when a surface-treated object with a good surface state is disposed in the inspection detector.

The seventh aspect of the present invention uses a technical means whereby in the surface property inspection method of the sixth aspect of the present invention, the initial threshold value Ethi is determined based on an average value EAav obtained by averaging output signals when multiple untreated objects are respectively disposed in the inspection detector, and an average value EBav obtained by averaging output signals when multiple treated object with a good surface state are respectively disposed in the inspection detector.

The eighth aspect of the present invention uses a technical means whereby in the surface property inspection method of the seventh aspect of the present invention, the initial threshold value Ethi is calculated according to the following formula where the standard deviation of output signals EA is σA and the standard deviation of output signals EB is σB.

$$Ethi=(EAav \cdot \sigma B+EBav \cdot \sigma A)/(\sigma A+\sigma B)$$

With the eighth aspect of the present invention, a high precision appropriate initial threshold value can be set using a small number of measurements.

The ninth aspect of the present invention uses a technical means whereby in the surface property inspection method of any one of the fifth through eighth aspects of the present invention, the evaluation apparatus comprises a memory device for storing each output signal when the surface property of each test object are inspected, and the threshold value is updated based on the stored output signals.

With the ninth aspect of the present invention, threshold values are updated based on output signals accumulated from a large number of test object inspections, therefore threshold value accuracy can be improved, enabling high accuracy inspections.

The tenth aspect of the present invention uses a technical means whereby in the surface property inspection method of any one of the fifth through ninth aspects of the present invention further includes an offset storage step for storing an output signal as initial offset values, the output signal is obtained with no test object placed in the inspection detector; wherein the placement step includes a step for acquiring output signals as inspection offset value prior to placement of the test object in the inspection detector; and wherein in the evaluation step, surface property of the test object is evaluated by correcting the output signal output from the AC bridge circuit based on the initial offset value and the inspection offset value, while the reference test object is disposed in the reference detector.

With the tenth aspect of the present invention, a high accuracy measurement, from which those effects are removed, can be performed even if the offset voltage changes due to changes in the measurement environment such as temperature, humidity, and magnetism.

The eleventh aspect of the present invention uses a technical means whereby in the surface property inspection method of the tenth aspect of the present invention, no inspection of the surface property of the test object is performed when a differential voltage, which is the difference between the initial offset value and the inspection offset value, exceeds an allowable value determined based on the surface property inspection device usage conditions.

With the eleventh aspect of the present invention, the inspection state can be monitored using the differential voltage between the initial offset value and the inspection offset, and an arrangement made so that no inspection of the surface properties of a test object is performed when said differential voltage exceeds an allowable value set based on surface property inspection device usage conditions.

The twelfth aspect of the present invention uses a technical means whereby in the surface property inspection method of any one of the fifth through eleventh aspects of the present invention, the evaluation apparatus comprises a memory device, and identifying information for each test object and surface property inspection data for said test objects are correlated and stored in said memory device.

With the twelfth aspect of the present invention of, identifying information for each test object such as lot, manufacturing number, and history can be stored in a manner correlating them to inspection data such as measurement value, pass/fail results, data measurement, and inspection status, so the surface treatment state of a test object which has been inspected by a surface property inspection device can be made traceable after distribution, ensuring traceability.

The thirteenth aspect of the present invention uses a technical means whereby in the surface property inspection method of any one of the fifth through twelfth aspects of the present invention, the evaluation step includes a step for detecting placement of the test object in the inspection detector based on changes in the signal output from the AC bridge circuit, and evaluation of the surface property of the test object is performed after the placement of the test object in the inspection detector is detected.

With the thirteenth aspect of the present invention, because evaluation of the surface properties of a test object can be started after detection of the state of placement of the test object in the inspection detector, measurement conditions can be made uniform and stable measurement values can be detected, such that variability caused by operators can be reduced and a high accuracy measurement performed.

The fourteenth aspect of the present invention uses a technical means whereby in the surface property inspection method of the thirteenth aspect of the present invention, the surface property inspection device comprises plurality of the inspection detector and a switching device, and the switching device switches the inspection detector after detecting that the test object has been removed from the inspection detector to which the AC bridge circuit is connected, wherein the removal of the test object is detected based on changes in the output signal from the AC bridge circuit.

With the fourteenth aspect of the present invention, because switching of the inspection detector is performed after detection that a test object has been removed from an inspection detector constituting a bridge circuit based on changes in a signal output from the AC bridge circuit, the inspection detector can be quickly and reliably switched and inspection efficiently and accurately performed.

The fifteenth aspect of the present invention uses a technical means whereby in the surface property inspection method of any one of the fifth through fourteenth aspects of the present invention, the surface property inspection device comprises plurality of the inspection detector and a switching device, the evaluation apparatus comprises a memory device, and the memory device correlates and stores identifying information for the inspection detectors which have inspected the test object with inspection data of the surface property for the test object.

With the fifteenth aspect of the present invention identifying information about an inspection detector which has inspected a test object, and surface property inspection data for the test object, can be correlated and stored.

Measurement value calibration and threshold values can thus be updated for each of the respective inspection detectors.

BRIEF DESCRIPTION OF FIGURES

FIG. 5 is a flowchart showing a measurement value calibration method.

FIG. 6(A) is an explanatory diagram showing changes in output value from placement of a test object through start of measurement.

FIG. 6(B) is an explanatory diagram showing changes in output values from the measurement completion through removal of the test object.

FIG. 7(A) is a flowchart showing the steps from placement of the test object up to start of measurement.

FIG. 7(B) is a flowchart showing the steps from measurement completion up to removal of the test object.

FIG. 9(A) is a flowchart showing a method for switching inspection detectors, executed in the order (A)→(B)→(C) in FIG. 9.

FIG. 9(C) is a flowchart showing a method for switching inspection detectors, executed in the order (A) (B) (C) in FIG. 9.

DETAILED DESCRIPTION OF PREFERRED EMBODIMENTS

First Embodiment (Surface Property Inspection Device)

Figure 1A:
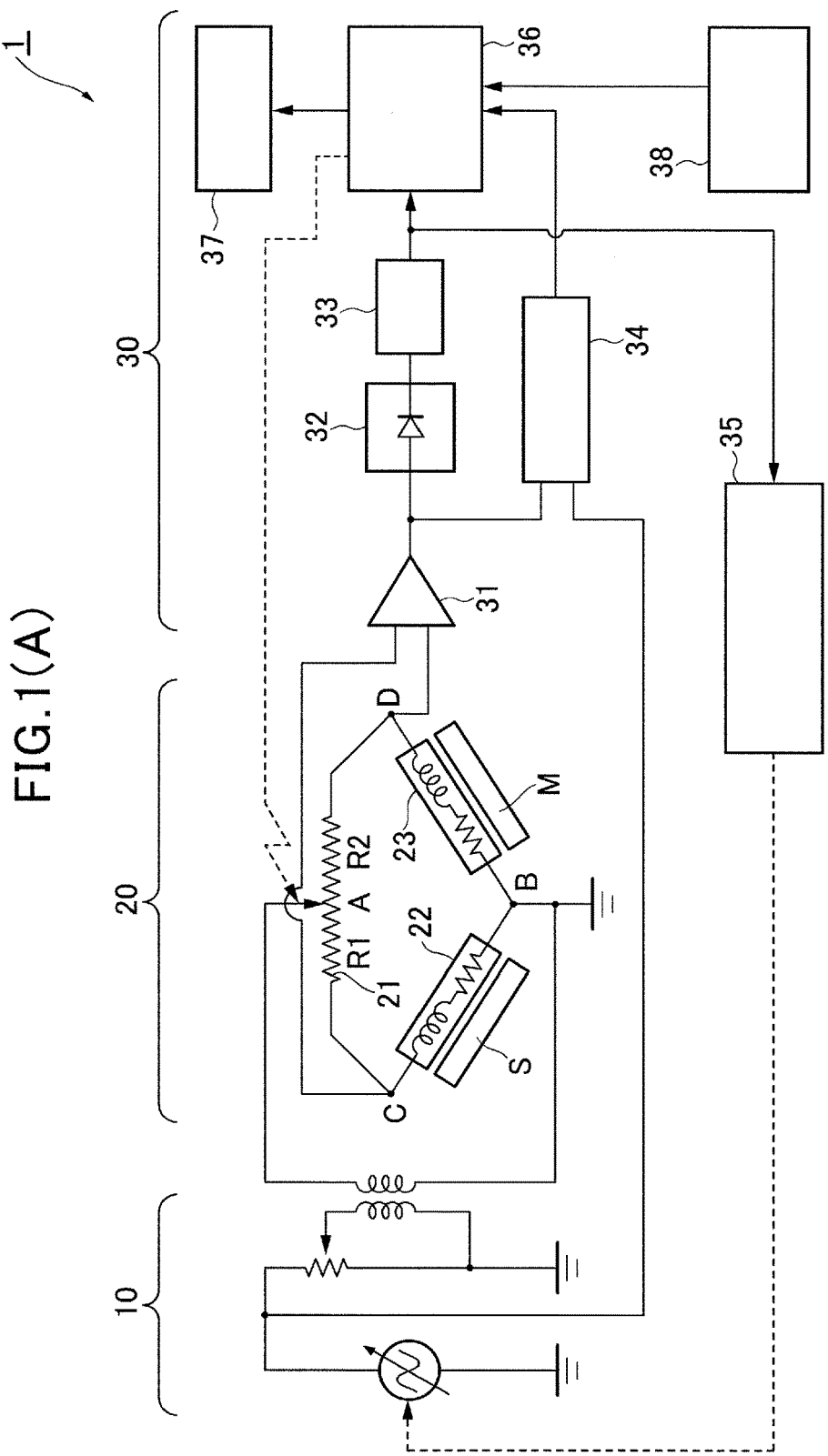
FIG. 1(A) is an explanatory drawing showing the circuit structure in a surface property inspection device.

As shown in FIG. 1(A), a surface property inspection device 1 according to an embodiment of the invention comprises an AC power supply 10, an AC bridge circuit 20, and an evaluation device 30.

The AC power supply 10 is capable of supplying variable frequency AC power to the AC bridge circuit 20.

The AC bridge circuit 20 is furnished with a variable resistor 21, a reference detector 22, an inspection detector 23 formed to permit placement of a coil to excite an eddy current in a test object M, and a reference detector 22 formed to permit placement of a reference test object S with the same structure as the test object M, for detecting a reference state serving as the basis for comparison with the output from the inspection detector 23. Here the word "same"

structure as the test object M" means the same materials and shape, regardless of whether or not subjected to surface treatment.

A variable resistor 21 is constituted to variably allocate the distribution ratio γ of a resistor RA to resistors R1 and R2. The resistor R1 and resistor R2, together with the reference detector 22 and the inspection detector 23, constitute a bridge circuit. In the present embodiment, point A dividing the resistor R1 and resistor R2, and point B between the reference detector 22 and the inspection detector 23, are connected to the AC power supply 10 in the evaluation device 30, and point C between the resistor R1 and the reference detector 22, and point D between the resistor R2 and the inspection detector 23, are connected to the amplifier 31. To reduce noise, the reference detector 22 and the inspection detector 23 sides are grounded.

The evaluation device 30 is furnished with an amplifier 31 for amplifying a voltage signal output from the AC bridge circuit 20, an absolute value circuit 32, a low-pass filter (LPF) 33, a phase comparator 34 for comparing phases between the AC voltage supplied from the AC power supply 10 and the voltage output from the amplifier 31, a frequency adjuster 35 for adjusting the frequency of the AC voltage supplied from the AC power supply 10, a judgment means 36 for performing a non-equilibrium adjustment to optimize the distribution between R1 and R2 and judge a pass/fail state of the surface of test object M based on the output from LPF 33, a display means 37 for displaying and warning of the judgment results by the judgment means 36, and a temperature measurement means 38 for detecting the temperature at the evaluation position. A memory device is also furnished inside the judgment means 36 or in an area not shown.

The amplifier 31 is connected to points C and D and receives an input of the difference in electrical potential between point C and point D. The absolute value circuit 32 and the LPF 33 are connected in that order to the judgment means 36. The phase comparator 34 is connected to the AC power supply 10, the amplifier 31, and the judgment means 36. The frequency adjuster 35 is connected to the AC power supply 10 and the amplifier 31. The judgment means 36, by outputting a control signal, can change the position of point A in the AC bridge circuit 20, i.e., it can change the distribution ratio r between resistor R1 and resistor R2; the variable resistance setting step described below is thus executed.

The temperature measurement means 38 comprises a non-contacting infrared sensor or thermocouple and outputs to the judgment means 36 a temperature signal for the surface of the test object M. When the temperature of the test object M detected by the temperature measurement means 38 is within a predetermined range, the judgment means 36 makes a pass/fail judgment of the surface treatment state of the test object M; when the temperature detected by the temperature measurement means 38 is outside a predetermined range, no pass/fail judgment is made of the surface treatment state of the test object M. This makes it possible not to perform a pass/fail judgment of the surface treatment state of the test object when the temperature of the test object M affects the accuracy of the inspection, so a high accuracy inspection can be performed. Here the evaluation position Ts may be measured by a thermocouple or the like, and a judgment made as to whether or not to make a pass/fail judgment of the surface property state of the test object M as a representative temperature for the temperature of the test object M.

As a reference detector 22 with the same constitution as the inspection detectors 23 and 23, a detector is formed in which a coil is wound around the outer perimeter of a core into which the evaluation portion of the test object M can be inserted, and the coil is placed opposite the surface of the test object M, brought into proximity therewith so that an eddy current in the test object M can be excited. I.e., the coil is wound to surround and oppose the surface property inspection area of the test object. Here, "surround the surface property inspection area of the test object" includes the meaning of exciting an eddy current in the surface property inspection area by enveloping (wrapping around) at least a portion of the surface property inspection area.

Figure 1B:
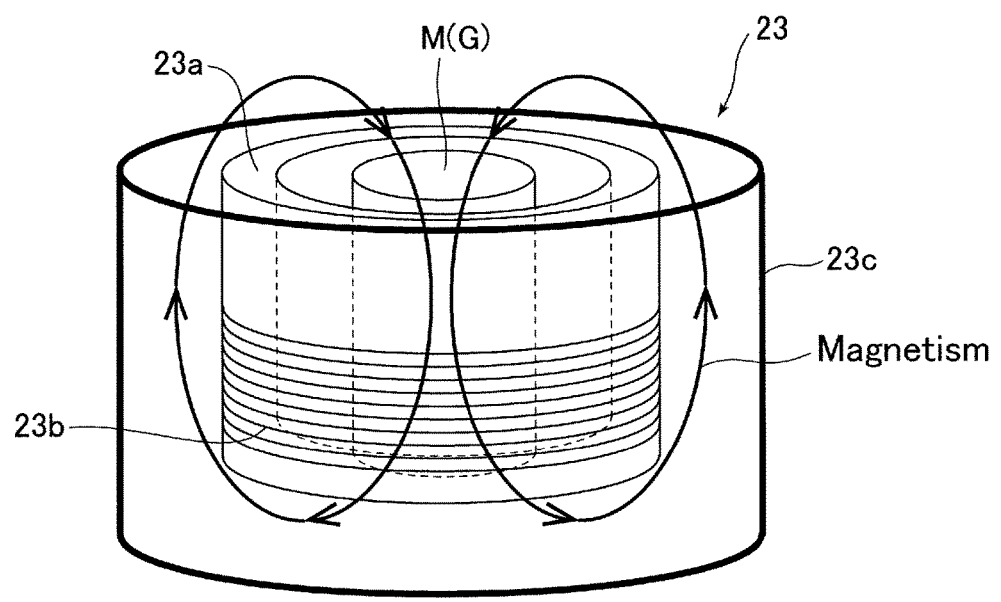
FIG. 1(B) is a perspective explanatory diagram showing the structure of an inspection detector.

Here we discuss a test object comprising a gear portion as a test object M, such as an inspection detector 23 used to inspect the surface properties of a gear G in which the gear portion has been surface treated. The inspection detector 23, as shown in FIG. 1(B), comprises a cylindrical core 23a formed to cover the gear portion of the gear G, and a coil 23b wound around the exterior perimeter surface of the core 23a. The core 23a is formed of a non-magnetic material, for example resin. Note that the shape of the core 23a is not limited to a cylinder so long as the gear G can be disposed within it. Note also that a reference inspection test object S for outputting a reference output may be placed without placing a test object M.

The inspection detector 23 has the feature that it captures eddy current reactions with high accuracy when evaluating surface properties, therefore it should preferably be disposed relative to the test object M so that eddy currents flow in the area where surface properties are to be inspected. I.e., it is preferable for the direction of windings in the coil 23b to be disposed in the same direction as the direction in which one wishes eddy currents to flow.

A residual stress layer is formed in the gear portion by shot-peening gear G. When evaluating gear G as a test object M, it is preferable to evaluate the surface properties of not only tooth tips, but also tooth surfaces and tooth bottoms. To do this, the winding direction of the coil 23b is disposed essentially perpendicular to the rotational axis of the gear G. Since a magnetic loop is generated in the rotational direction, this enables an eddy current to be excited in the rotational direction of the gear G, so that not only the tooth tip, but also the tooth surface and tooth bottom can be evaluated. Conventional contacting detectors required multiple types of detector to be prepared to fit the shape of the tooth being inspected, and surface properties close to the contacting portion could not be inspected, but using the inspection detector 23, a broad range of surface properties can be inspected at once with a single detector.

The inspection detector 23 does not have to be furnished with a core 23a so long as the coil 23b can maintain a shape. Such a coil 23b may be formed, for example, by adhesion of an enamel copper wire wound on an air core using a hardening epoxy resin or the like, or by winding around an air core using a heat-hardening fusing enamel copper wire, then hardening with heat from hot air or a drying oven.

The inspection detector 23 is disposed so that the coil 23h opposes and surrounds the surface of the test object M to be inspected; an AC magnetic field is generated when AC power at a predetermined frequency is supplied to the coil 23b by the AC power supply 10, and an eddy current flowing in a direction crossing the AC magnetic field is excited on the surface of the test object M. Since eddy currents change in response to electromagnetic properties of the residual stress layer, the phase and amplitude (impedance) of the output waveform output from the amplifier 31 changes in response to properties of the residual stress layer (the surface treatment state). Electromagnetic properties of the surface treatment layer can be detected using these changes in output waveform to perform an inspection.

It is also possible to provide a magnetic shield 23c, disposed outside the inspection detector 23 and surrounding the test object M. External magnetism is blocked by using the magnetic shield 23e, therefore detection sensitivity to electromagnetic properties can be improved, and detection sensitivity to electromagnetic properties corresponding to surface treatment state improves, so the surface treatment state of a test object M can be more accurately evaluated.

(Output from AC Bridge Circuit)

Figure 2:
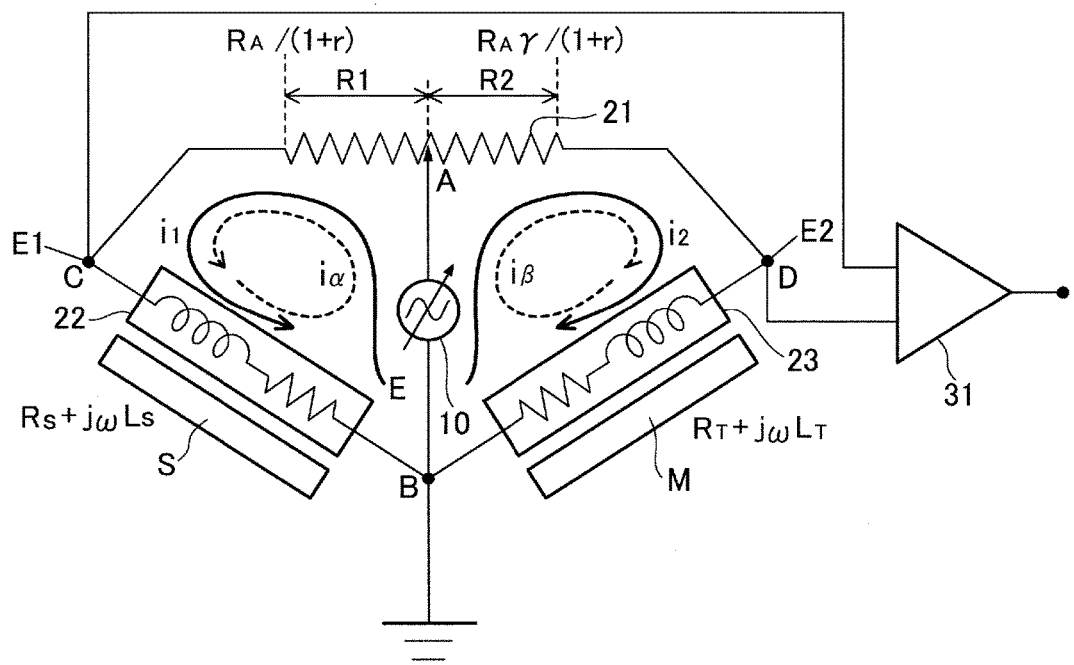
FIG. 2 is an equivalent circuit diagram explaining the output from an AC bridge circuit.

Next, referring to the equivalent circuit in FIG. 2, we explain the output from the AC bridge circuit 20, adjusted to a non-equilibrium state. A reference test object S for outputting a reference output is placed in close proximity to the reference detector 22, and the test object M for which a pass/fail determination of the surface treatment state is required is placed in close proximity to the inspection detector 23. Here the reference test object S has the same structure as the test object M, and preferably uses an untreated part on which no surface treatment has been performed.

If the distribution ratio of variable resistor RA is $\gamma$, resistor R1 is $R_A/(1+\gamma)$, and resistor R2 is $R_A\gamma/(1+\gamma)$. The benchmark detector 22 impedance is considered to be $R_S+j\omega L_S$, and the impedance of the inspection detector 23 is considered to be $R_T+j\omega L_T$.

Assuming an electrical potential E at point A, the excitation currents flowing on each side of the bridge with each test piece (reference test object S, test object M) not placed in proximity to the reference detector 22 and the inspection detector 23, are respectively $i_1$ and $i_2$; the degree of magnetism is changed by placing each test object in proximity to the reference detector 22 and the inspection detector 23, and the currents flowing in response to the degree of that change are respectively $i\alpha$ and $i\beta$. The electrical potentials E1, E2 and excitation currents $i_1$, $i_2$ of the reference detector 22 and the inspection detector 23 at this time are expressed by the formulas in Expressions (1) through (4).

Exp. 1:
$$E1 = (R_S + j\omega L_S)(i\alpha + i_1) \quad (1)$$

Exp. 2:
$$E2 = (R_T + j\omega L_T)(i\beta + i_2) \quad (2)$$

Exp. 3:
$$i_1 = \frac{E}{\frac{R_A}{1+\gamma} + R_S + j\omega L_S} \quad (3)$$

Exp. 4:
$$i_1 = \frac{E}{\frac{R_A\gamma}{1+\gamma} + R_T + j\omega L_T} \quad (4)$$

The voltage output to the amplifier 31 is the differential between E1 and E2, and is expressed by the following formula.

Exp. 5:
$$E2-E1=[\{(R_T+j\omega L_T)i\beta-(R_S+j\omega L_S)i\alpha\}+\{(R_T+j\omega L_T)i_2-(R_S+j\omega L_S)\}] \quad (5)$$

The following expression is derived from Expressions (3) through (5).

Exp. 6:
$$E2 - E1 = \left[ \{(R_T + j\omega L_T)i\beta - (R_S + j\omega L_S)i\alpha\} + \left\{(R_T + j\omega L_T)\frac{E}{\frac{R_A\gamma}{1+\gamma} + R_T + j\omega L_T} - (R_S + j\omega L_S)\frac{E}{\frac{R_A}{1+\gamma} + R_S + j\omega L_S}\right\} \right] \quad (6)$$

We will consider each of the differential voltage components by separating the right side of Expression (6) into the following components A and B.

Component A:
$$(R_T + j\omega L_T)i\beta - (R_S + j\omega L_S)i\alpha$$

Component B:
$$(R_r + j\omega L_T)\frac{E}{\frac{R_A\gamma}{1+\gamma} + R_T + j\omega L_T} - (R_S + j\omega L_S)\frac{E}{\frac{R_A}{1+\gamma} + R_S + j\omega L_S}$$

Component A comprises each of the detector components: ($R_S+j\omega L_S$), ($R_T+j\omega L_T$), and the electrical current amounts, which change when each of the test objects is placed in proximity to each detector: $i\alpha$ and $i\beta$. The sizes of $i\alpha$ and $i\beta$ vary with the amount of magnetism passing through the test object due to electromagnetic properties such as magnetic permeability and electrical conductivity. For this reason, the size of $i\alpha$ and $i\beta$ can be changed by changing the excitation currents $i_1$, $i_2$ which control the amount of magnetism generated by each detector. According to Expressions (3) and (4), excitation currents $i_1$, $i_2$ change according to the variable resistor distribution ratio $\gamma$, therefore the size of component A can be changed by adjusting the variable resistor distribution ratio $\gamma$.

Component B comprises each of the detector components: ($R_S j\omega L_S$), ($R_T+j\omega L_T$), and the resistance parameter divided by the variable resistor distribution ratio $\gamma$. Therefore the size of component B can be changed by adjusting the variable resistor distribution ratio $\gamma$ in the same way as for component A.

When the test object M is disposed at a predetermined position and AC power at a predetermined frequency is supplied to the coil 23b in the inspection detector 23 by the AC power supply 10, an eddy current flowing in a direction crossing the AC magnetic field is excited on the surface of the test object M. Since eddy currents change in response to electromagnetic properties of the residual stress layer, the phase and amplitude (impedance) of the output waveform output from amplifier 31 changes in response to properties of the residual stress layer (the surface treatment state). Electromagnetic properties of the residual stress layer can be detected using these changes in output waveform to perform an inspection of the surface treatment layer.

Signals output from the bridge amplifier 31 are signals which extract the differential surface area between the reference detector 22 and inspection detector 23 voltage waveforms, and form a circuit for holding fixed the current flowing in the detector (excitation current). The extracted voltage signal can also be thought of as power signal. Power supplied to the detector is always constant. Magnetic energy supplied to the test object M can in this way be kept constant.

(Surface Property Inspection Method)

Figure 3:
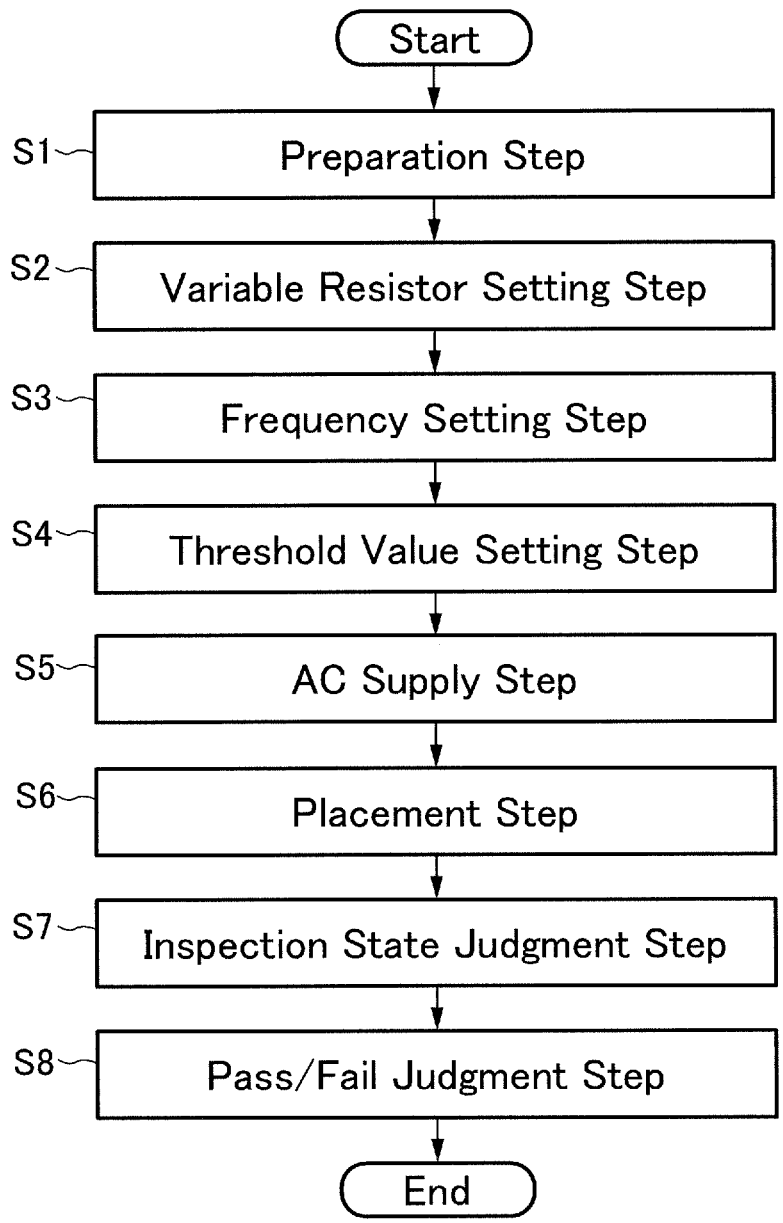
FIG. 3 is a flowchart showing a surface property inspection method.

Next, referring to FIG. 3, we explain a method for inspecting the surface properties of a test object using a surface property inspection device 1.

First, the surface property inspection device 1 and a reference test object S are prepared in preparatory step S1.

Next, a variable resistor setting step S2 is performed.

In variable resistor setting step S2, AC power is first supplied from the AC power supply 10 to the AC bridge circuit 20. In this state, the distribution ratio γ of the variable resistor 21 is adjusted to achieve a high test object detection accuracy by the surface property inspection device 1. I.e., the distribution ratio γ of the variable resistor 21 is adjusted so that the output signal of the AC bridge circuit 20 is reduced without placing the test object in proximity to the inspection detector 23. By thus setting the variable resistor 21, the difference in output signal is increased between the case when the surface treatment state of a test object M brought into proximity with the inspection detector 23 is poor and the case when the surface treatment state is good, and detection accuracy can be raised. Specifically, the voltage amplitude of the output signal from the AC bridge circuit 20 or the voltage output from the LPF 33 are monitored using a display device with a waveform display function such as an oscilloscope (e.g., the one comprising judgment means 36), and the distribution ratio γ is adjusted to reduce the output. The distribution ratio γ of variable resistor 21 is preferably adjusted and set so that the output reaches a minimum value or a local minimum value (local equilibrium point).

Adjustment of the variable resistor 21 distribution ratio γ is performed in order to improve inspection accuracy by increasing the output difference corresponding to the difference in surface states by reducing the differential voltage (E2−E1). As described above, components A and B are changed by adjusting the distribution ratio γ, therefore the variable resistor 21 distribution ratio γ can be adjusted in response to the impedance $(R_S+j\omega L_S)$ and $(R_T+j\omega L_T)$ of the reference detector 22 and the inspection detector 23, and the differential voltage (E2−E1), which is the output from the AC bridge circuit 20, can be reduced. Thus the difference in properties between the reference detector 22 and the inspection detector 23 can be reduced and at least a little more of the inherent properties of the test object M can be extracted, improving detection accuracy.

In frequency setting step S3, AC power is supplied from the AC power supply 10 to the AC bridge circuit 20 with the reference test object S brought into proximity with the inspection detector 23; the frequency of AC power supplied to the AC bridge circuit 20 by the frequency adjuster 35 is varied, and the voltage amplitude output from the AC bridge circuit 20 or the voltage output from the LPF 33 are monitored.

The frequency adjuster 35 outputs a control signal to the AC power supply 10 to achieve an initial frequency f1 set in frequency adjuster 35, and the output voltage Ef1 from the amplifier 31 at a frequency 11 is input to the frequency adjuster 35 and stored. Next, a control signal is output to the AC power supply 10 to reach a frequency f2, which is higher than frequency f1 by a predetermined value, such as 100 Hz; an output voltage Ef2 from the amplifier 31 at frequency f2 is input to the frequency adjuster 35 and stored.

Next, Ef1 and Ef2 are compared; if Ef2>Ef1, a control signal is output to reach a frequency f3, which is higher by a predetermined value than frequency f2; an output voltage Ef3 from the amplifier 31 at frequency f3 is input to the frequency adjuster 35 and stored. Ef2 and Ef3 are then compared. This is repeated, and the frequency fn when Efn+1<Efn, i.e. the frequency fn at which output is maximum, is set as the frequency used in the frequency setting step S4 and the AC supply step S5. This enables setting of a frequency by a one-time operation to cause the output from the AC bridge circuit 20 to increase in response to objects under test M with differing surface treatment states or shapes and differing impedances. Optimal frequency changes depending on the material, shape, and surface treatment state of the test object, but when these are known in advance, setting the frequency is unnecessary. Thus a sensitive response to changes in the surface treatment state is possible, and inspection sensitivity can be improved.

Here the frequency setting step S3 can also be executed before the variable resistor setting step S2.

The threshold value used to judge the quality of the test object M surface state is set in the threshold value setting step S4. Here we explain a method for pre-setting the threshold value ("initial threshold value" below) for use at the start of evaluation of a test object M. First, the reference test object S is placed in proximity to the reference detector 22, and AC power at a frequency set in the frequency setting step S3 is supplied from the AC power supply 10 to the AC bridge circuit 20. The voltage output from the AC bridge circuit 20 is amplified by the amplifier 31; full wave rectification is performed by the absolute value circuit 32; a DC conversion is performed in the LPF 33, and the result is output to the judgment means 36. From ten to multiple tens of untreated objects under test and surface-treated objects under test with a good surface state are respectively prepared, and output value distribution data is acquired from the output values output to the judgment means 36 when the respective test objects are placed in proximity to the inspection detector 23. This is shown schematically in FIG. 4.

The initial threshold value Ethi is determined by the following expression, with consideration for the variability of the respective output signals, based on the output signal EA when an untreated test object M is placed in the inspection detector 23, and on the output EB when a treated test object M with a good surface state is placed in the inspection detector 23.

Figure 4:
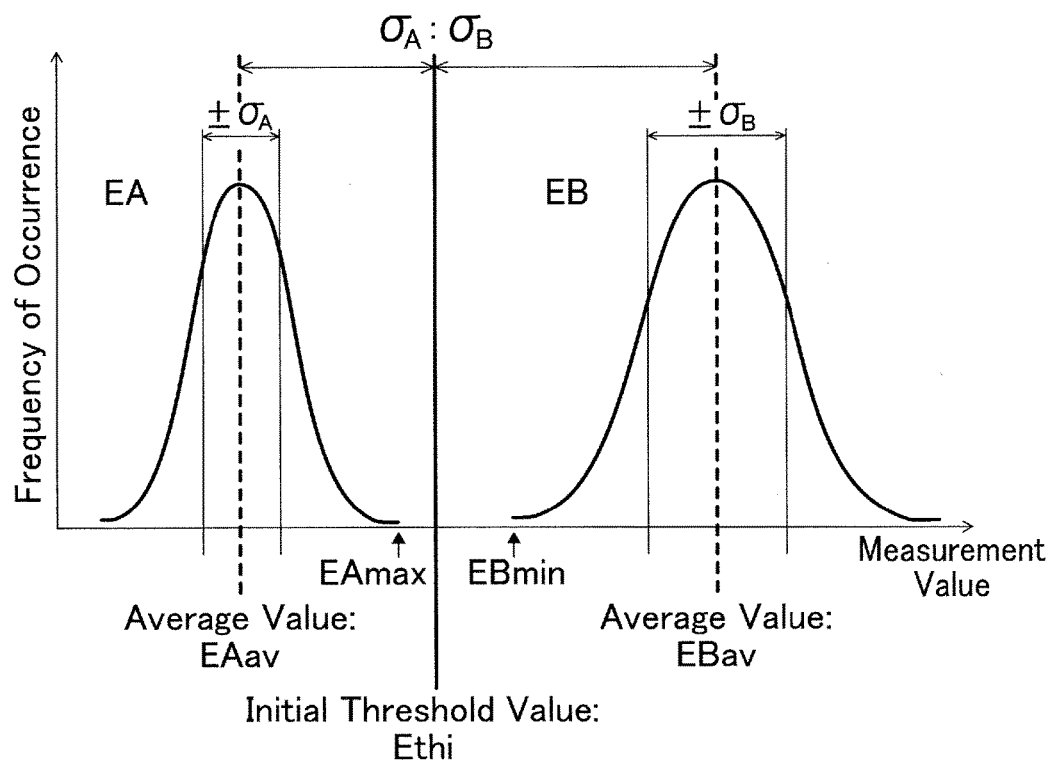
FIG. 4 is a diagram explaining a method for setting an initial threshold value.

The distribution between output signal EA from the untreated test object and output signal EB from the treated test object is shown schematically in FIG. 4.

$$Ethi=(EAav\cdot\sigma B+EBav\cdot\sigma A)/(\sigma A+\sigma B) \quad \text{Exp. 7:}$$

EAav: average value of output signal EA; EBav: average value of output signal EB; σA: standard deviation in output signal EA; σB: standard deviation in output signal EB.

A high accuracy appropriate threshold value can thus be set with a small number of measurements. This initial value Ethi is set as an initial value and stored in the judgment means 36. Here the initial threshold value Ethi has the relationship EAmax<Ethi<Ebmin between the maximum value EAmax of the output signal EA and the minimum value EBmin of the output signal EB.

Note that even when the relationship above is not satisfied, an appropriate initial threshold value Ethi can be set by taking into account factors such as variability in the output signal EA and output signal EB, and whether there are unique measurement values greatly divergent from the distribution, etc. For example, there is a method whereby multiple measurements are performed on the untreated state and the surface treated state of the same objects under test, and using the initial threshold value Ethi is re-computed.

In addition, in threshold value setting step S4 an output signal with the test object M not in proximity to the inspection detector 23 is stored in the judgment means 36 as initial offset value Ei.

In AC supply step S5, AC power at the frequency set in frequency setting step S3 is supplied from the AC power supply 10 to the AC bridge circuit 20. Here the reference test object S is proximate to the reference detector 22.

Next, in placement step S6, the test object M for which a surface treatment state pass/fail determination is to be made is placed in proximity to the inspection detector 23 and disposed in such a way that an eddy current is excited in the test object M. At this point a voltage output signal is output from the AC bridge circuit 20; the output signal is amplified by the amplifier 31, full wave-rectified by the absolute value circuit 32, and converted to DC by the LPF 33.

Before the test object M is proximate to the inspection detector 23, or after placement of the test object M, the surface temperature of the test object M is measured and a surface temperature signal for the test object M is output to the judgment means 36.

In test state judgment step S7, the phase comparator 34 compares the AC power waveform supplied from the AC power supply 10 with the AC voltage waveform output from the AC bridge circuit 20 to detect their phase difference. By monitoring this phase difference, a judgment can be made as to whether or not the inspection state is good (e.g., there is no positional offset between the inspection detector 23 and the test object M). Even if the outputs from the AC bridge circuits 20 are the same, the inspection state changes when there are large changes in phase difference, and a judgment can be made that the inspection may not be being correctly implemented. In addition, when the temperature of the test object M detected by the temperature measurement means 38 is within a predetermined range, the judgment means 36 makes a pass/fail judgment of the test object M surface treatment state; when the temperature detected by temperature measurement means 38 is outside a predetermined range, no pass/fail judgment is made of the surface treatment state of the test object M. Here the predetermined temperature range is the temperature range in which changes in the test object M temperature exert no substantive effect on the inspection; it can be set, for example, to 0 to 60° C. Various measures can be undertaken when the temperature of the surface of test object M is outside a predetermined temperature range, such as placing the system in standby, or blowing air onto the test object M, or moving the test object M to a different line without testing it, until the test object M falls within a predetermined temperature range.

In the pass/fail judgment step S8, the signal converted to DC by LPF 33 is input to the judgment means 36; the judgment means 36 judges the quality of the surface state of the test object M based on the inputted signal. I.e., this step is an evaluation step for evaluating the surface properties of a test object NI based on an output signal from the AC bridge circuit 20. The judgment results by the judgment means 36 are displayed by the display means 37, and if the surface state is poor, a warning is issued.

A judgment of the test object M surface treatment pass/fail state is made by comparing the output value (measurement value) from the LPF 33 with the threshold value set in threshold setting step S4. If the output value (measured value) from the LPF 33 exceeds the threshold value, the judgment means 36 judges that the surface state is good; if the output value (measured value) from the LPF 33 is below the threshold value, the judgment means 36 judges that the surface state is poor.

Inspection data such as measured value, pass/fail judgment result, date of measurement, and inspection state (temperature, humidity, differential voltage ΔE described below, etc.) are correlated with lot, production number, history, or other information identifying each test object M and stored in the evaluation apparatus 30 judgment means 36 or in a memory device not shown. I.e., identifying marks associated with each of the measurement data can be directly or indirectly appended to the test object. For example, a bar code or product control number associated with measurement data can be directly or indirectly displayed. By associating measurement data in this way to identifying markings such as bar codes, product control numbers, etc., the surface state of a test object inspected by a surface property inspection device can be tracked after distribution, thereby assuring traceability.

With the above-described steps, a pass/fail test of the surface treatment state of test object M can be performed easily and with high accuracy. To continue the test, it is sufficient to swap only the test object M and repeat placement step S6, test state judgment step S7, and pass/fail judgment step S8. If the type of test object M or the type of surface treatment etc. is changed, variable resistor setting step S2, frequency setting step S3, and threshold setting step S4 are again performed.

The inspection detector 23, by capturing changes in the eddy current flowing on the surface of a test object M, can indirectly capture changes in surface resistance.

Here, if shot-peening is performed as the surface treatment, causes for changes in eddy current include deformations, structural refinement, or dislocation caused by shot-peening, but under the temperature changes occurring within the measurement environment (0° C.~40° C.), these are essentially fixed. Magnetic changes detected by the inspection detector 23 are caused by changes in the demagnetized field of eddy current flow, and since changes in eddy current flow are little affected by temperature changes in the measurement environment, effects on test accuracy from temperature changes can be minimized.

Because a reference test object of the same structure as the test object M is used to detect a reference state in the reference detector 22, fluctuations in output values due to changes in the inspection environment such as temperature, humidity, and magnetism, will be the same on the reference detector as on the test object M.

Fluctuations in output values caused by changes in the inspection environment such as temperature, humidity, or magnetism can thus be canceled and measurement accuracy improved. As in the third aspect of the present invention, use of an untreated part to which no surface treatment has been applied as the reference test object S enables the output, which is based on the difference in surface state relative to the test object M, to be increased, therefore measurement accuracy can be still further improved and the threshold value more easily set, making this preferable.

(Threshold Value Update Setting)

If there is a large difference between the output signal EA when an untreated test object M is placed in the inspection detector 23 and the output signal EB when a surface treated test object M with a good surface state is placed in the inspection detector 23, the initial threshold value Ethi may approach the average value EAav side of the output signal EA, and the range of the output deemed to indicate good product may increase. Therefore if one wishes to set a still more accurate threshold value, the threshold value can be reset based on a large amount of inspection data accumulated by repeated measurements using the initial threshold value Ethi. The newly set threshold value in this instance is referred to as updated threshold value Ethn.

Setting of the updated threshold value Ethn is performed after inspecting 100 or more objects under test M. An example of the method for setting an updated threshold value Ethn is shown below. Here the output signal from a test object M inspected using an initial threshold value Ethi shall be EC; the minimum value thereof shall be ECmin, maximum value ECinax, average value ECav, and standard deviation σC.

In one method, the initial threshold value Ethi and minimum value ECmin are compared, and the updated threshold value Ethn calculated as follows.

If ECmin≤Ethi, the initial threshold value Ethi is used without setting the updated threshold value Ethn.

If ECmin>Ethi, ECmin can be set as the updated threshold value Ethn.

It is also possible, using average value ECav and standard deviation σC, to adopt ECav-3 σC or ECav-4 σC for the updated threshold value Ethn. Which of ECav-3 σC or ECav-4 αC to use should be judged with consideration for the distribution of the output signal EC; when ECav-3 σC or ECav-4 σC is equal to or less than initial threshold value Ethi, initial threshold value Ethi is used without setting an updated threshold value Ethn.

Updated threshold value Ethn can also be set based on the relative sizes of the minimum value ECmin, maximum value ECmax, and average value ECav. Specifically, cases are distinguished by comparing the average value of minimum value ECmin and maximum value ECmax (ECmin+ECmax)/2 with the average value ECav.

If (ECmin+ECmax)/2≤ECav: set ECav-3 σC as updated threshold value Ethn.

If (ECmin+ECmax)/2>ECav: set ECav-4 σC as updated threshold value Ethn.

Here, if ECav-3 σC or ECav-4 σC is equal to or less than the initial threshold value Ethi, initial threshold value Ethi is used without setting an updated threshold value Ethn.

The updated threshold value Ethn can be repeatedly updated based on inspection data for objects under test M inspected after an update.

For example, inspection of 100 objects under test M could be performed after setting the initial threshold value Ethi, then inspection of a further 100 objects under test M performed after setting updated threshold value Ethn, then a new updated threshold value Ethn set based on that inspection data. A new updated threshold value Ethn could also be set using inspection data for all 200 objects.

(Measurement Calibration)

Measurements can be calibrated using the aforementioned initial offset value Ei and inspection offset value Eik.

As shown in FIG. 5, in step S101 inspection offset value Eik is measured and stored in the judgment means 36 before placement of a test object M in step S6.

In step S102 which follows, the initial offset value Ei and the inspection offset value Eik are compared and a differential voltage ΔE=Ei−Eik is calculated. Step S102 and beyond correspond to the pass/fail judgment step S8.

Inspection of the test object M is performed in step S103 and a measurement value (E2−E1) stored in step S104; differential voltage ΔE is added to the stored measurement value in step S105.

In step S106, the measurement value to which the differential voltage ΔE is added is compared to a threshold value to make a pass/fail judgment.

By this means, even if the offset voltage changes due to changes in the measurement environment such as temperature, humidity, and magnetism, a high accuracy measurement, from which those effects are removed, can be performed. I.e., an appropriately high accuracy measurement can be performed with calibration carried out each time on the measuring equipment (inspection device).

If the differential voltage ΔE exceeds the allowable value set based on surface property inspection device 1 usage conditions, a judgment can be made that the inspection state is inappropriate, such as when there are large disturbances or apparatus problems, so that inspection may not be being appropriately performed. In this case it is possible not to inspect the surface properties of the test object M in inspection state judgment step S7. On such occasions the reference detector 22 and inspection detector 23 may be checked, the temperature of the measurement environment confirmed, the reference test object S checked or replaced, etc. The subject allowable values can be set as conditions for appropriate performance of an inspection; e.g., as 5% of the initial offset value Ei(ΔE=0.05Ei).

(Control of Unit Under Test Placement and Extraction)

The placement of the test object M in the inspection detector 23 and removal from the inspection detector 23 can be controlled using the measurement value En (En=E2−E1).

Referring to FIGS. 6 and 7, we now explain a method for controlling placement and removal of a test object. Note that FIG. 6 shows an example to explain the initial offset value Ei0 and output value En, and is shown schematically, so is not an actual output value.

First, when a test object M is placed in the inspection detector 23 in step S201 shown in FIG. 7(A), the output value begins to decline starting at initial offset value Ei0=3.000 when no test object M is placed, as shown in FIG. 6(A).

Next, in step S202, placement of the test object M in the inspection detector 23 is detected; and a trigger for the criterion to start the time count, which starts recording output values (start of the wait for measurement in FIG. 6(A)), is detected.

In FIG. 6(A), the time at which the output value reaches 1.500 is deemed to be placement complete wait trigger En1; this counts waiting time in step S203. Note that the output value (1.500) which becomes the placement complete wait trigger En1 is set by a reverse calculation so that the output value is stable when a predetermined time explained in the following paragraph has elapsed.

Upon the elapse of a predetermined waiting time until the output value stabilizes (e.g., 2 to 3 seconds), measurement is performed in step S204 and a stable output value En2 (0.370) is detected and stored.

Since this enables a detection of the state of placement of the test object M in the inspection detector 23, i.e. of the fact that the test object M has been placed in a state whereby inspection can be appropriately performed so that evaluation of test object surface properties can begin, measurement conditions can be made uniform and a stable output value En2 detected, and operator-caused variability, etc. can be eliminated and high accuracy measurement performed.

Control of removal of the test object M is performed as follows.

First, when a test object M is removed from an inspection detector 23 in the step S30 shown in FIG. 7(B), the measurement value starts to rise from the output value En2 observed when the test object M is placed, as shown in FIG. 6(B).

Next, in step S302, the removal completion wait trigger En3, which serves as the criterion (the start of completion wait in FIG. 6(B)) for starting a count of the wait time to confirm removal of the test object, is detected. In FIG. 6(B), wait time is counted in step S303, using the time when the measurement value reaches 2.500 as the removal completion wait trigger En3. Note that the output value (2.500) for the removal completion wait trigger En3 is set by reverse calculation so that the output value becomes stable when the predetermined wait time described in the following paragraph elapses.

When a predetermined wait time (e.g., 2 to 3 seconds) until the measurement value recovers to the vicinity of the initial value Ei0 has elapsed, the output value Ei1 (3.000) is detected in step S304 and stored. At this point, the stored output value Ei1 can be used as the inspection offset value Eik.

In this manner, the fact that the test object M has been removed can be detected, and the next measurement performed with the measurement value returned to the initial state.

Using an arrangement in which control of placement and removal of a test object M is performed as described above, an apparatus can be simply constituted without the need to provide a position sensor or the like to detect whether a test object M has been appropriately placed relative to an inspection detector 23. Also, by adopting a system combining a transport means for transporting the test object M from a surface treatment apparatus for performing surface treatment to the surface property inspection device 1 (e.g., a conveyor belt), or sorting means for sorting inspected objects under test M into good and bad parts, everything from surface treatment to inspection of the test object M can be performed consistently, and an automatable system can be built.

(Variant Examples)

When inspection state judgment step S7 is not implemented, the surface property inspection device 1 can omit the phase comparator 34. For example, a configuration can be used in which the positional relationship between the inspection detector 23 and the test object M is performed by a position detection means such as a laser displacement gauge, and a determination made using an optoelectric sensor (laser) or the like of whether the offset between the inspection detector 23 axis and the test object M axis are within a predetermined range. The phase comparator 34, frequency adjuster 35, or display means 37 can be integrated into a single piece by, for example, building them into the judgment means 36.

If the output from the AC bridge circuit 20 at the time of the test object M measurement is sufficiently large, the variable resistor setting step S2 and frequency setting step S3 may be omitted. If the frequency setting step S3 is omitted, the surface property inspection device 1 can omit the frequency adjuster 35.

Effect of the First Embodiment

Using the surface property inspection device 1 and surface property inspection method of the present invention, an eddy current is excited in test object M by the coil 23b of inspection detector 23, and the surface properties of test object M can be evaluated by comparing the output signal output from the AC bridge circuit 20 with a threshold value. This enables high precision inspection of the surface state using a simple circuit configuration.

Because a reference test object S of the same structure as the test object M is used to detect a reference state in the reference detector 22, even if output values fluctuate due to changes in inspection environment such as temperature, humidity, and magnetism, the effects thereof will be the same on the test object M. Fluctuations in output values caused by changes in the inspection environment such as temperature, humidity, or magnetism can thus be canceled and measurement accuracy improved. As in the third aspect of the present invention, use of an untreated part to which no surface treatment has been applied as the reference test object S enables the output, which is based on the difference in surface state relative to the test object M, to be increased, therefore measurement accuracy can be still further improved and the threshold value more easily set, which is preferable.

It is also possible to further improve measurement accuracy by setting an appropriate threshold value or calibrating a measurement value using an offset value.

Second Embodiment

Figure 8:
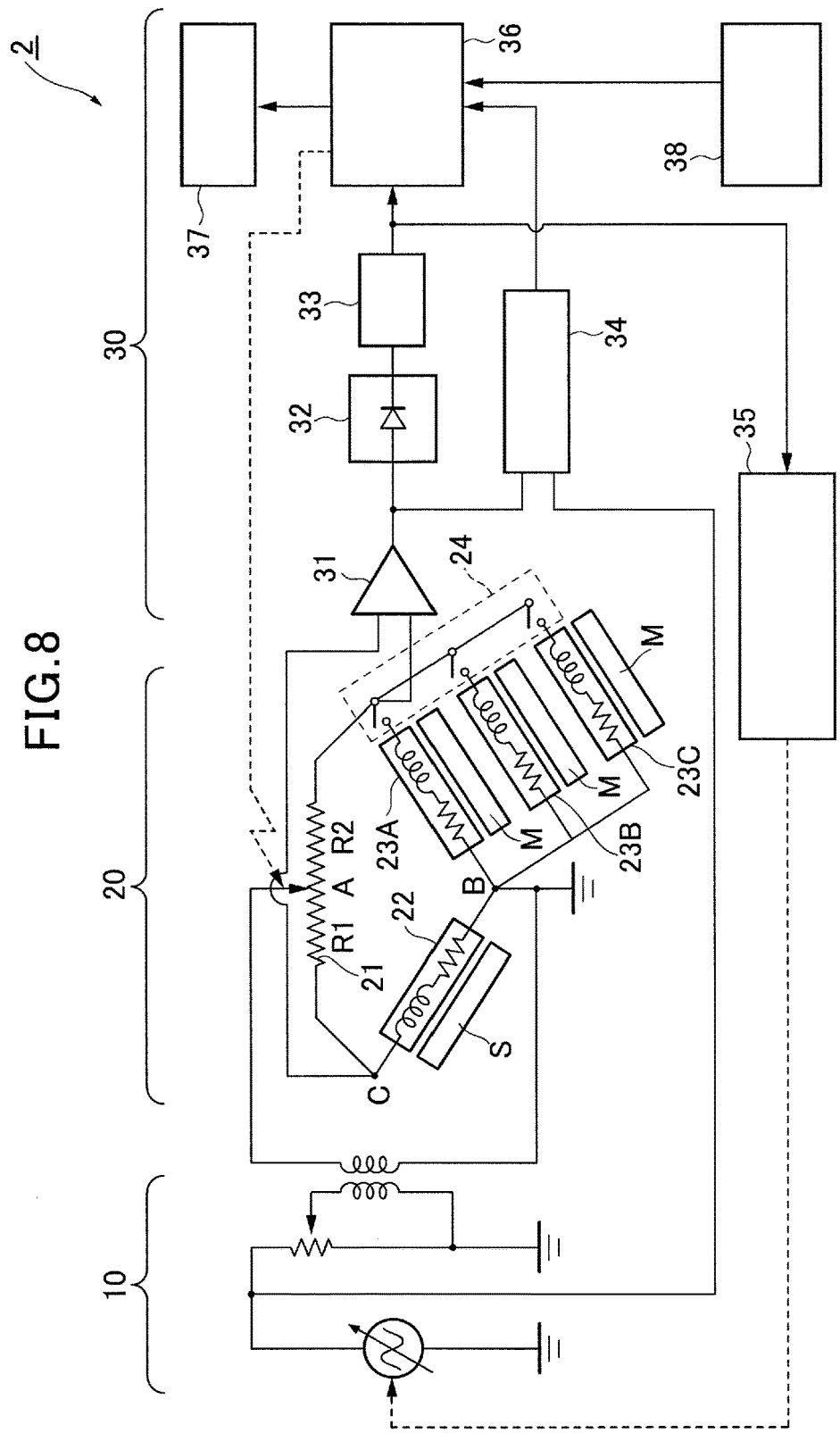
FIG. 8 is an explanatory diagram showing the circuit configuration for a surface property inspection device according to a second embodiment.

It is also possible, as in the surface property inspection device 2 of FIG. 8, to adopt a constitution in which the AC bridge circuit 20 comprises multiple inspection detectors 23.

Here a constitution is shown in which there are three inspection detectors: 23A. 23B, and 23C.

The inspection detectors 23A. 23B, and 23C are configured so that each can be connected through a switching device 24 to the AC bridge circuit 20. Using the evaluation apparatus 30 judgment means 36, the switching device 24 has the function of switching so that one of the inspection detectors 23A, 23B, and 23C, together with the resistor R2 and the reference detector 22, form an AC bridge circuit 20; for example, digital circuit elements such as analog switches or mechanical switches such as toggle switches can be used.

Figure 9B:
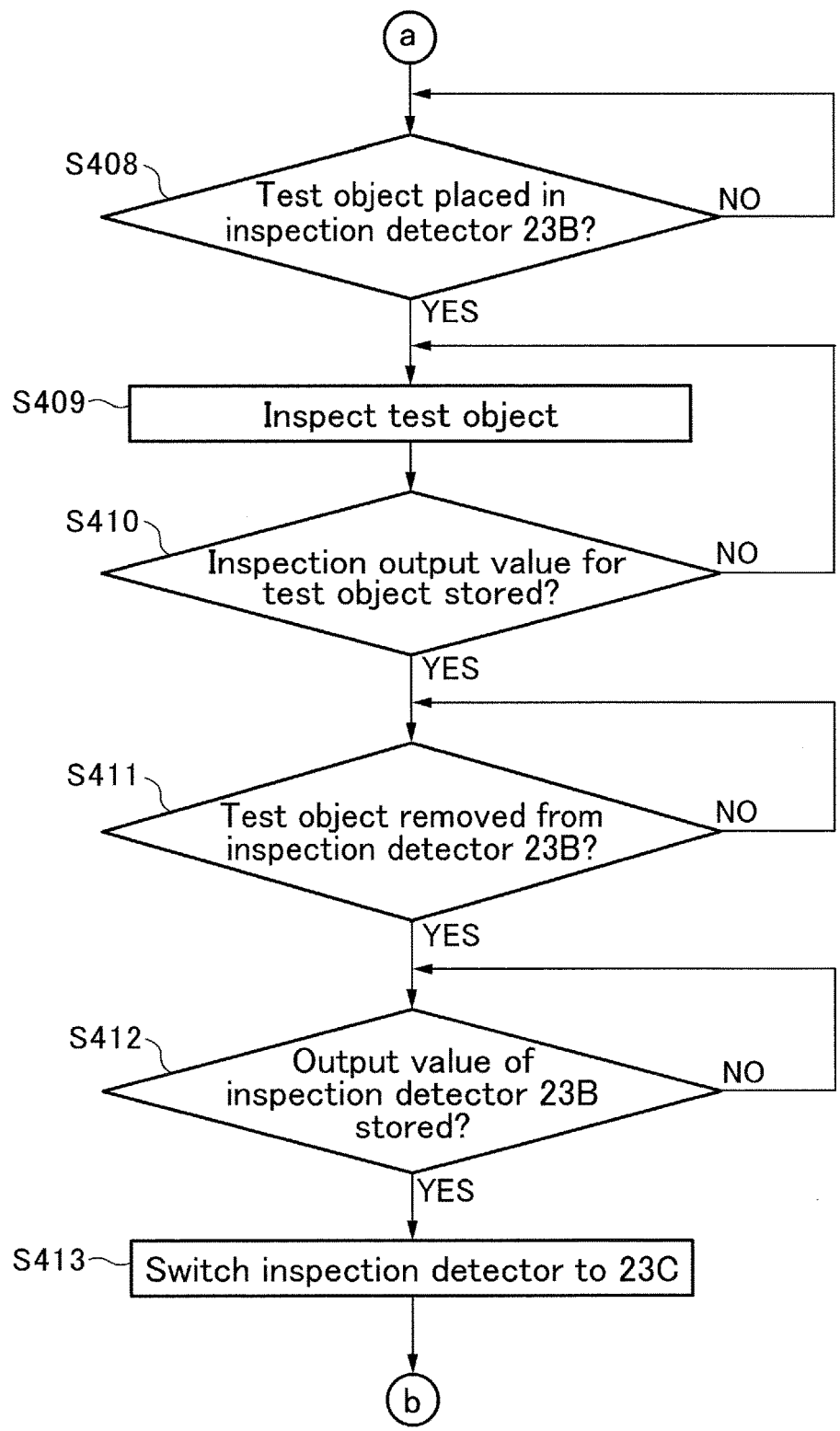
FIG. 9(B) is a flowchart showing a method for switching inspection detectors, executed in the order (A)→(B)→(C) in FIG. 9.

Switching of the inspection detectors 23A, 23B, and 23C by the switching device 24 is performed using the following steps. FIGS. 9(A), (B), and (C) are flow charts showing steps for switching in the order of inspection detector 23A→inspection detector 23B→inspection detector 23C, and are executed in the order (A)→(B)→(C) in FIG. 9. FIG. 10 is an explanatory diagram showing the state of placement of objects under test M in the inspection detectors 23A, 23B, and 23C.

The inspection detectors 23A, 23B, and 23C are pre-adjusted in steps S2 through S4 shown in FIG. 3. Here it is possible to repeat steps S2 through S4 to set each inspection detector, such that in inspection detector 23A, after steps S2 through S4 have been performed there is a switch to the inspection detector 23B and steps S2 through S4 are again performed, or setting can be performed by executing each step while switching inspection detectors 23A, 23B, and 23C.

First, in the initial state the inspection detector 23A is connected to form a bridge circuit.

In step S401, transport of the test object M is started by the transport means.

Figure 10A:
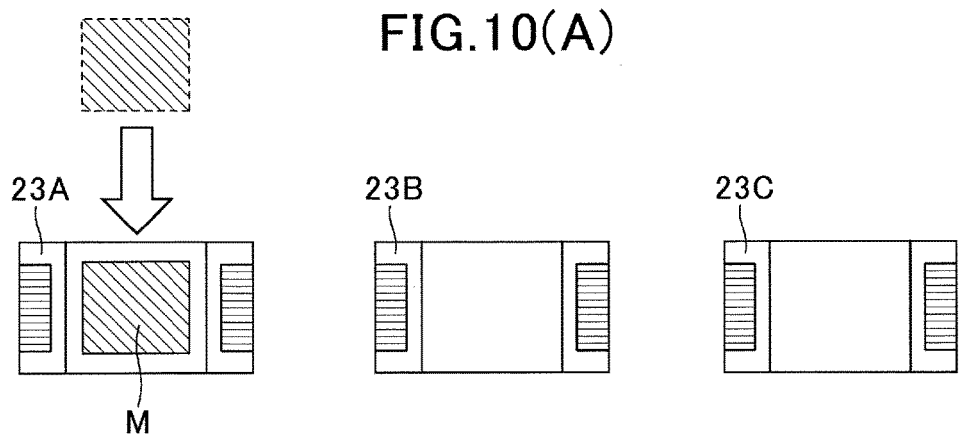
FIG. 10 is an explanatory diagram schematically showing the transport of objects under test to multiple inspection detectors.

First, as shown in FIG. 10(A), the test object M is transported to the inspection detector 23A.

In the ensuing step S402, a judgment is made as to whether the test object M transported to the inspection detector 23A is placed in the inspection detector 23A. The judgment as to whether the test object M is placed in the inspection detector 23A is made by detecting the placement completion wait trigger shown by step S202 in FIG. 7(A).

If there is a YES judgment in step S402, the test object M has been placed in the inspection detector 23A, so the system advances to step S403, and an inspection of the test object M is performed and an output value stored. Here step S403 corresponds to step S204 in FIG. 7(A). The output value is stored in association with information as to whether an inspection was done by the inspection detector. Here the output value is stored in association with information (inspection detector identifying information) that an inspection was done by the inspection detector 23A.

If a NO judgment is made in step S402, the test object M is not placed in the inspection detector 23A, so the system stands by until the test object M is placed in the inspection detector 23A.

In step S403 the test object M is inspected; in the ensuing step S404 a judgment is made as to whether a test object M inspection output value has been stored.

If a YES judgment is made in step S404, a test object M inspection detector value is stored, so the system advances to step S405.

If a NO judgment is made in step S404, a test object M inspection detector value is not stored, so the system returns to step S403.

In the succeeding step S405 a judgment is made as to whether the test object M has been removed from the inspection detector 23A, The judgment as to whether the test object has been removed from the inspection detector 23A is made by detection of the removal completion wait trigger shown in step S302 of FIG. 7(B), and by counting the wait time in step S303.

If a YES judgment is made in step S405, the test object NI is removed from the inspection detector 23A, so the system advances to step S406.

If a NO judgment is made in step S405, the test object M is not removed from the inspection detector 23A, so the system stands by until the test object M is removed from the inspection detector 23A.

In step S406, the output value is differentiated from the other inspection detectors 23B and 23C, as shown in step S304, and a judgment is made as to whether this was stored as the output value for the inspection detector 23A.

If a YES judgment is made in step S406, the inspection detector 23A output value is stored, so the system advances to step S406.

If a NO judgment is made in step S406, the inspection detector 23A output value is not stored, so the system stands by until the output value of the inspection detector 23A is stored.

In step S407, the inspection detector 23 forming the bridge circuit 30 is switched from the inspection detector 23A to the inspection detector 23B by the switching device 24.

As described above, conditions to satisfy for switching the inspection detector 23A to the inspection detector 23B are that after inspection of the test object M has ended, the test object NI has been removed from the inspection detector 23A; and that the output value after the test object M has been removed from the inspection detector 23A has been stored.

Figure 10B:
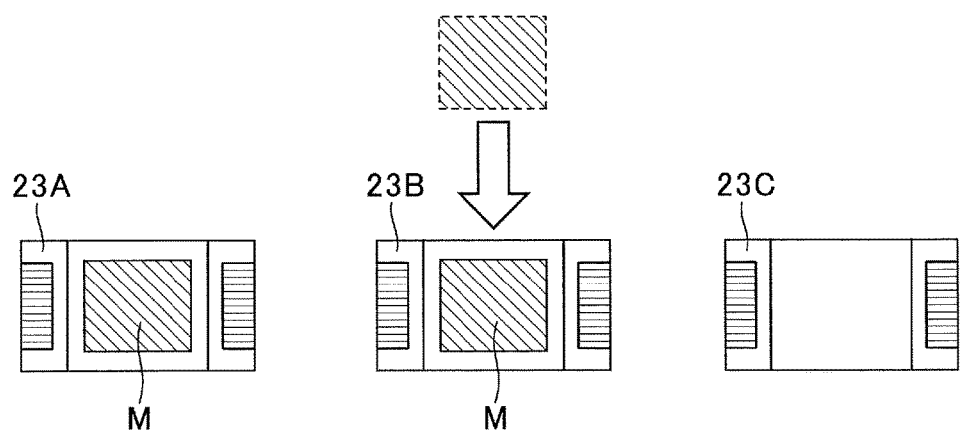

Here, during the time processing is being executed up until step S407, or after execution, a new test object M is carried into the inspection detector 23B, as shown in FIG. 10(B).

In steps S408 to S412, treatment is executed in the same way as in steps S402 through S406 with respect to the switched inspection detector 23B.

If a YES judgment is made in step S412, inspection of the test object M ends, the test object M is removed from the inspection detector 23B, and the output value is stored so the system advances to step S413 and the inspection detector 23 constituting evaluation apparatus 30 is switched by the switching device 24 from the inspection detector 23B to the inspection detector 23C.

Note that the output value of the test object M inspected by the inspection detector 23B and the output value of the inspection detector 23B alone are correlated to the inspection detector 23B and stored.

Figure 10C:
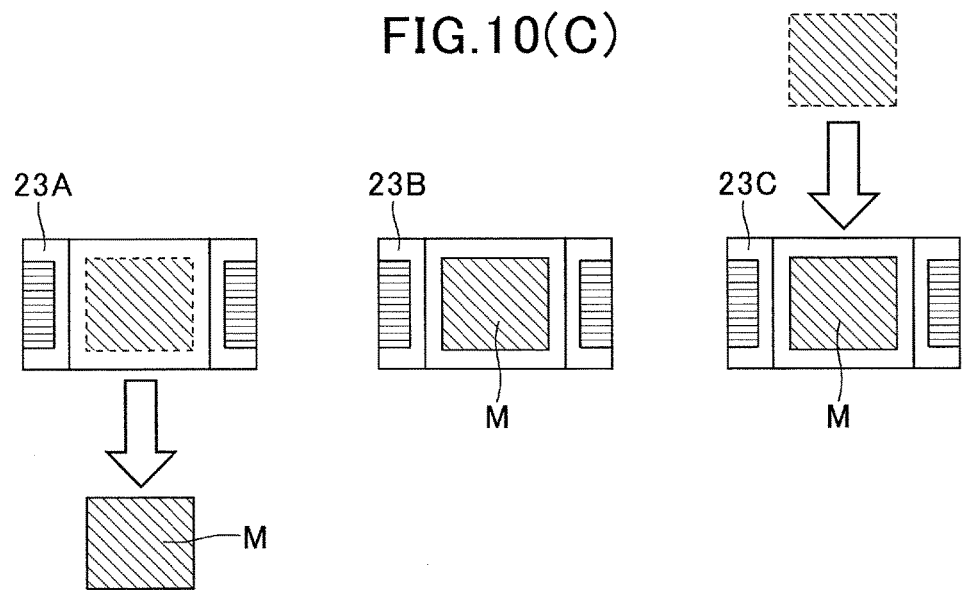

During the treatment up until step S413, or after treatment, a new test object M is carried into the inspection detector 23C, as shown in FIG. 10(C).

In steps S414 to S418, treatment is performed in the same way as in steps S402 through S406 with respect to the switched inspection detector 23C.

If a YES judgment is made in step S418, inspection of the test object M ends, the test object M is removed from the inspection detector 23C, and the output value is stored, so the system advances to step S419 and the inspection detector 23 constituting evaluation the apparatus 30 is switched by the switching device 24 from the inspection detector 23C to the inspection detector 23A.

In addition, the output value of the test object M inspected by the inspection detector 23C and the output value of the inspection detector 23C alone are correlated to the inspection detector 23C and stored.

Continuing, it is sufficient when performing an inspection of the test object M to repeat the steps from step S402 forward.

The above-described surface property inspection device 2 and surface property inspection method comprise multiple inspection detectors 23; continually arriving objects under test W are placed in the inspection detectors 23; inspection detectors 23 constituting an AC bridge circuit 20 are switched by the switching device 24 and inspections are performed in sequence, so the time required from transport through to completion of inspection can be shortened. In addition, because the AC power supply 10 and the evaluation apparatus 30 are shared and there is no requirement to prepare multiple surface property inspection device stands, equipment cost can be reduced. Because of the shared use of the reference test object S, there is no need to consider the effects of fluctuations in output value caused by variability among reference inspection objects S.

Since switching of the inspection detectors 23A, 23B, and 23C is performed based on the output from each inspection detector, switching can be done quickly and reliably to perform inspection efficiently and accurately.

Also, because the results of inspecting objects under test M and output values from only the inspection detectors 23A, 23B, and 23C are stored in correlation with identifying information for the inspection detectors 23A, 23B, and 23C, calibration of the measurement values shown in FIG. 5, and setting of a new threshold value Ethn, can be performed for the inspection detectors 23A, 23B, and 23C, respectively.

(Variant Examples)

In the present embodiment we disclosed a constitution with three inspection detectors 23, but the invention is not limited thereto, and a constitution comprising the necessary number of inspection detectors 23 may be adopted. In FIG. 10, inspection detectors 23A, 23B, and 23C are shown schematically, and are disposed apart from one another, but other forms may be adopted in which they are integrally disposed, as in a rack or the like.

In the present embodiment, setting of the inspection detectors 23A, 23B, and 23C was performed in steps S2 through S4, but if there is a guarantee of device differences between the inspection detectors 23A, 23B, and 23C, is possible to set any one of those and share use of those setting conditions.

FIG. 10 shows a form in which a test object M is successively transported to the inspection detectors 23A, 23B, and 23C, but the invention is not limited thereto; for example, objects under test M could be simultaneously transported to the inspection detectors 23A, 23B, and 23C.

Effect of the Second Embodiment

Using the surface property inspection device 2 and surface property inspection method of the second embodiment, the following effects can be provided in addition to those provided by the surface property inspection device 1 and surface property inspection method of the first embodiment.

The surface property inspection device 2 comprises multiple inspection detectors 23, and switching of the inspection detectors 23 constituting the AC bridge circuit 20 can be performed by the switching device 24 to perform sequential inspections, thus shortening the time required from transport through completion of inspection. In addition, because the AC power supply 10 and evaluation apparatus 30 are shared, and there is no requirement to prepare multiple surface property inspection device stands, equipment cost can be reduced.

Since switching of the inspection detectors 23A, 23B, and 23C is performed based on the output from each inspection detector, the inspection detectors 23 can be switched quickly and reliably to perform inspection efficiently and accurately.

What is claimed is:

1. A method for inspecting surface property, comprising steps of:
providing the surface property inspection device for inspecting surface property of a test object subjected to surface treatment, comprising: an alternating current bridge circuit an alternating current power supply for supplying alternating current power to the alternating current bridge circuit and an evaluation apparatus for evaluating the surface property of the test object based on an output signal from the alternating current bridge circuit wherein the alternating current bridge circuit has a variable resistor capable of varying the distribution ratio between a first resistor and a second resistor, an inspection detector comprising a coil capable of exciting alternating current magnetism and formed so that said coil excites an eddy current in the test object, and a reference detector constituted to excite the eddy current in a reference test object having the same structure as the test object for detecting a reference state serving as a reference for comparison with the output from the inspection detector, whereby the first resistor, the second resistor, the reference detector, and the inspection detector constitute the alternating current bridge circuit and wherein the evaluation apparatus evaluates surface property of the test object by comparing an output signal from the alternating current bridge circuit with a predetermined threshold value while alternating current power is supplied to the alternating current bridge circuit, the inspection detector detects electromagnetic property of the test object, and the reference detector detects the reference state; the method further comprising:
a placement step for placing the inspection detector at a predetermined position relative to the test object so that the eddy current is excited in the test object when alternating current power is supplied from the alternating current power supply to the alternating current bridge circuit; and
an evaluation step for evaluating surface property of the test object by comparing an output signal output from the alternating current bridge circuit with the threshold value while the reference test object is disposed in the reference detector;
wherein the placement step and the evaluation step are executed for each test object,
wherein an initial threshold value Ethi is used as the threshold value when starting evaluation of the test object, the initial threshold value Ethi is determined based on an output signal EA obtained when an untreated object is disposed in the inspection detector, and an output signal EB obtained when a surface-treated object with a good surface state is disposed in the inspection detector,
wherein the initial threshold value Ethi is determined based on an average value EAav obtained by averaging output signals when multiple untreated objects are respectively disposed in the inspection detector, and an average value EBav obtained by averaging output signals when multiple treated object with a good surface state are respectively disposed in the inspection detector, and
wherein the initial threshold value Ethi is calculated according to the following formula where the standard deviation of output signals EA is σA and the standard deviation of output signals EB is σB $$Ethi=(EAav\cdot\sigma B+EBav\cdot\sigma A)/(\sigma A+\sigma B).$$

2. The method of claim 1, wherein the evaluation apparatus comprises a memory device for storing each output signal when the surface property of each test object are inspected, and the threshold value is updated based on the stored output signals.

3. The method of claim 1, further comprising an offset storage step for storing an output signal as initial offset values, the output signal is obtained with no test object placed in the inspection detector;
wherein the placement step includes a step for acquiring output signals as inspection offset value prior to placement of the test object in the inspection detector; and
wherein in the evaluation step, surface property of the test object is evaluated by correcting the output signal output from the alternating current bridge circuit based on the initial offset value and the inspection offset value, while the reference test object is disposed in the reference detector.

4. The method of claim 3, wherein no inspection of the surface property of the test object is performed when a differential voltage, which is the difference between the initial offset value and the inspection offset value, exceeds an allowable value determined based on the surface property inspection device usage conditions.

5. The method of claim 1, wherein the evaluation apparatus comprises a memory device, and identifying information for each test object and surface property inspection data for said test objects are correlated and stored in said memory device.

6. The method of claim 1, wherein the evaluation step includes a step for detecting placement of the test object in the inspection detector based on changes in the signal output from the alternating current bridge circuit, and evaluation of the surface property of the test object is performed after the placement of the test object in the inspection detector is detected.

7. The method of claim 6, wherein the surface property inspection device comprises plurality of the inspection detector and a switching device, and the switching device switches the inspection detector after detecting that the test object has been removed from the inspection detector to which the alternating current bridge circuit is connected, wherein the removal of the test object is detected based on changes in the output signal from the alternating current bridge circuit.

8. The method of claim 1, wherein the surface property inspection device comprises plurality of the inspection detector and a switching device, the evaluation apparatus comprises a memory device, and the memory device correlates and stores identifying information for the inspection detectors which have inspected the test object with inspection data of the surface property for the test object.

* * * * *

UNITED STATES PATENT AND TRADEMARK OFFICE
CERTIFICATE OF CORRECTION

PATENT NO. : 9,964,520 B2
APPLICATION NO. : 15/112473
DATED : May 8, 2018
INVENTOR(S) : Yoshiyasu Makino et al.

Page 1 of 1

It is certified that error appears in the above-identified patent and that said Letters Patent is hereby corrected as shown below:

In the Claims

Claim 1, Column 21, Line 46, insert a --;-- between "circuit" and "an"

Signed and Sealed this
Fourteenth Day of May, 2019

Andrei Iancu
*Director of the United States Patent and Trademark Office*